(12) United States Patent
Gray

(10) Patent No.: US 9,446,199 B1
(45) Date of Patent: Sep. 20, 2016

(54) SYRINGE AND METHOD OF USING

(76) Inventor: Robin Scott Gray, Ellicott City, MD (US)

( * ) Notice: Subject to any disclaimer, the term of this patent is extended or adjusted under 35 U.S.C. 154(b) by 1033 days.

(21) Appl. No.: 12/925,183

(22) Filed: Oct. 15, 2010

Related U.S. Application Data

(62) Division of application No. 11/640,648, filed on Dec. 18, 2006, now Pat. No. 7,842,017, which is a division of application No. 10/949,016, filed on Sep. 24, 2004, now Pat. No. 7,175,609, which is a division of application No. 10/057,519, filed on Jan. 24, 2002, now Pat. No. 6,830,564.

(51) Int. Cl.
*A61M 5/315* (2006.01)
*A61M 5/31* (2006.01)
*A61M 5/50* (2006.01)

(52) U.S. Cl.
CPC ........... *A61M 5/3137* (2013.01); *A61M 5/502* (2013.01); *A61M 2005/3121* (2013.01); *A61M 2005/3139* (2013.01)

(58) Field of Classification Search
CPC ......... A61M 5/3137; A61M 5/31513; A61M 5/5013; A61M 5/502; A61M 2005/3131
USPC .............. 604/68, 70, 90, 110, 111, 131, 134, 604/135, 195, 198, 218, 232, 244, 221, 222
See application file for complete search history.

(56) References Cited

U.S. PATENT DOCUMENTS

| | | | | |
|---|---|---|---|---|
| 577,682 A | * | 2/1897 | Eissner | 604/222 |
| 1,838,039 A | * | 12/1931 | Montuori | 604/220 |
| 1,950,717 A | * | 3/1934 | Douglas | 439/713 |
| 2,678,647 A | * | 5/1954 | Bruger | 604/227 |
| 2,771,880 A | * | 11/1956 | Gotthart | 604/221 |
| 3,128,765 A | * | 4/1964 | Tint | 604/193 |
| 3,134,340 A | | 5/1964 | Armao | |
| 3,376,866 A | * | 4/1968 | Ogle | 604/203 |
| 3,760,503 A | * | 9/1973 | Baskas | 433/90 |
| 3,885,297 A | * | 5/1975 | Tischlinger | 29/450 |

(Continued)

*Primary Examiner* — Kevin C Sirmons
*Assistant Examiner* — William Carpenter
(74) *Attorney, Agent, or Firm* — Robin S. Gray

(57) ABSTRACT

Syringes and methods of using are described which protect the syringe barrel cavity from contaminants. A first syringe is formed with a corrugated sheath which encloses the plunger and space between the rearward end face surface of the syringe barrel handle member and the forward face of the plunger handle member. A second syringe is formed with a syringe barrel having a straight segment and a corrugated segment having the forward face of the plunger handle member molded to the rearward terminus of the corrugated segment of the syringe barrel. A third syringe is formed from mating syringe barrel and plunger member walls. The walls of the mating syringe barrel and plunger member are concentric and slide relative to each other while maintaining an enclosure around the plunger shaft. A fourth syringe is formed from inner and outer concentric syringe barrel walls mating with the walls of a plunger member. The mating walls are concentric and slide relative to each other while maintaining an enclosure around the plunger shaft. A fifth syringe is formed with an end cap contaminant shield having an extension wall that is mated with the rearward end opening of the syringe barrel cavity. Alternatively, the end cap contaminant shield can be provided with a flat design without the extending wall and is bonded or molded to the rearward end terminus of the syringe barrel. The end cap contaminant shield designs are provided with an opening defining the shape of the cross-section of the plunger shaft.

20 Claims, 9 Drawing Sheets

(56) References Cited

U.S. PATENT DOCUMENTS

| | | | |
|---|---|---|---|
| 4,030,498 A * | 6/1977 | Tompkins | A61M 5/31513 604/152 |
| 4,068,662 A | 1/1978 | Sneider | |
| 4,072,149 A * | 2/1978 | Tischlinger | 604/202 |
| 4,753,638 A | 6/1988 | Peters | |
| 4,804,371 A | 2/1989 | Vaillancourt | |
| 4,911,694 A | 3/1990 | Dolan | |
| 4,915,697 A | 4/1990 | Dupont | |
| 4,927,416 A * | 5/1990 | Tomkiel | 604/198 |
| 4,932,947 A | 6/1990 | Cardwell | |
| 4,946,441 A | 8/1990 | Laderoute | |
| 5,017,187 A | 5/1991 | Sullivan | |
| 5,019,053 A * | 5/1991 | Hoffman et al. | 604/220 |
| 5,219,338 A | 6/1993 | Haworth | |
| 5,259,840 A * | 11/1993 | Boris | 604/110 |
| 5,419,766 A | 5/1995 | Chang et al. | |
| 5,419,773 A | 5/1995 | Kupp | |
| 5,509,903 A * | 4/1996 | Grendahl et al. | 604/187 |
| 5,527,297 A | 6/1996 | Paul | |
| 5,554,125 A * | 9/1996 | Reynolds | A61J 1/062 604/187 |
| 5,607,399 A * | 3/1997 | Grimard et al. | 604/220 |
| 5,782,815 A * | 7/1998 | Yanai et al. | 604/218 |
| 5,817,047 A | 10/1998 | Osborn, III et al. | |
| 5,833,660 A * | 11/1998 | Nathan et al. | 604/110 |
| 5,961,472 A * | 10/1999 | Swendson et al. | 600/573 |
| 5,997,514 A * | 12/1999 | Balestracci | 604/227 |
| 6,224,561 B1 * | 5/2001 | Swendson et al. | 600/562 |
| 6,248,094 B1 * | 6/2001 | Epperson | 604/195 |
| 6,280,418 B1 * | 8/2001 | Reinhard | A61M 5/28 604/181 |
| 2003/0065291 A1 * | 4/2003 | Corrigan, Jr. | 604/199 |
| 2004/0254539 A1 * | 12/2004 | Wolbring et al. | 604/187 |
| 2007/0106226 A1 * | 5/2007 | Croll et al. | 604/199 |

* cited by examiner

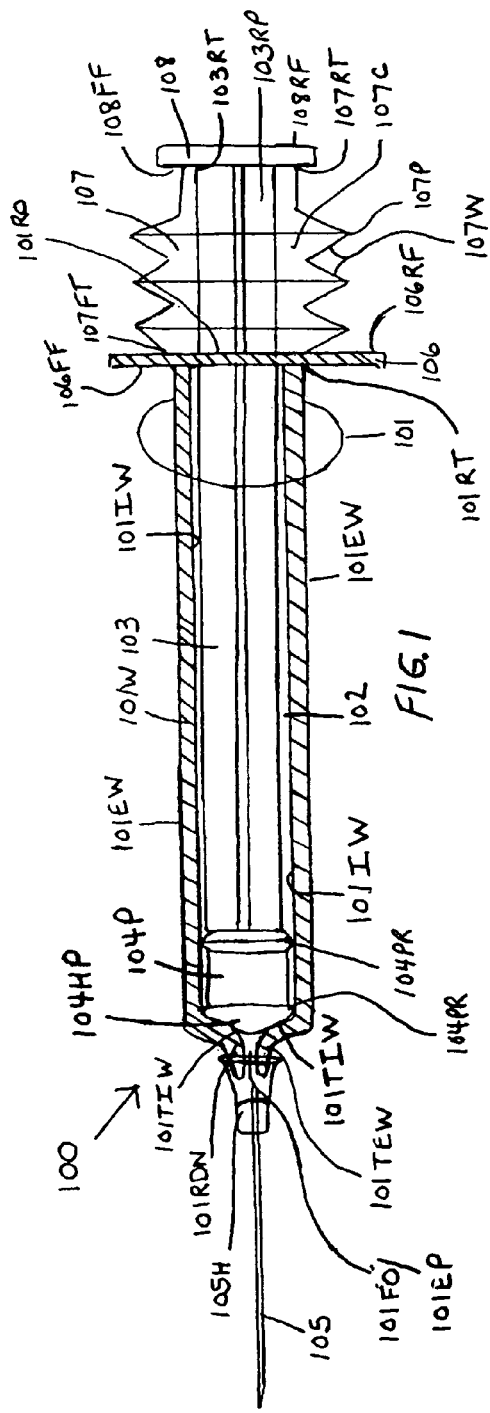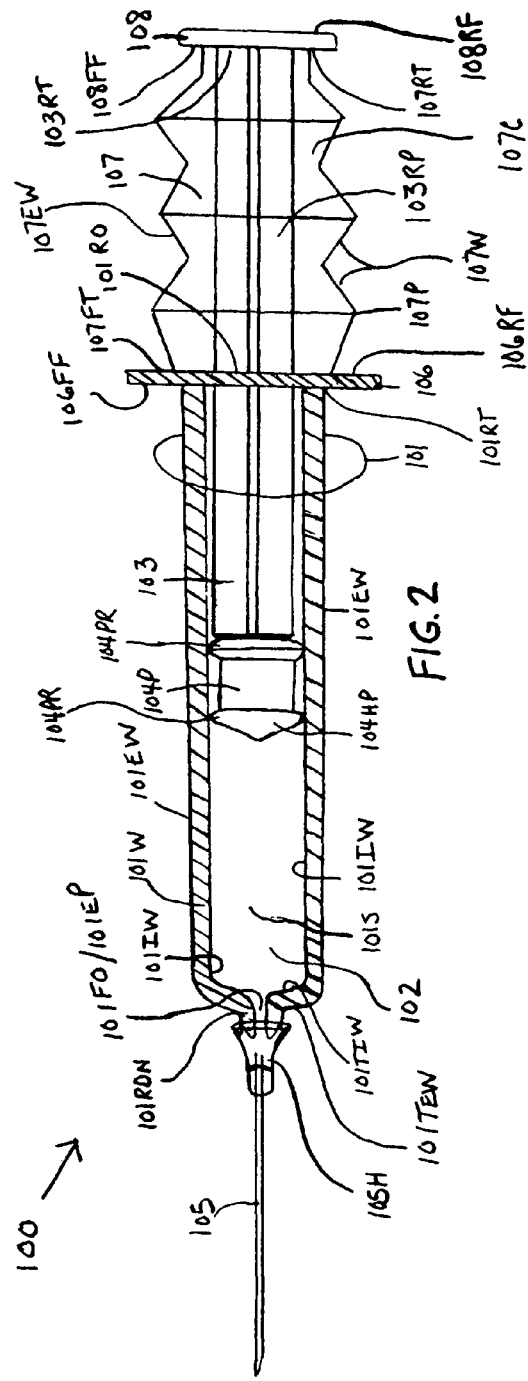

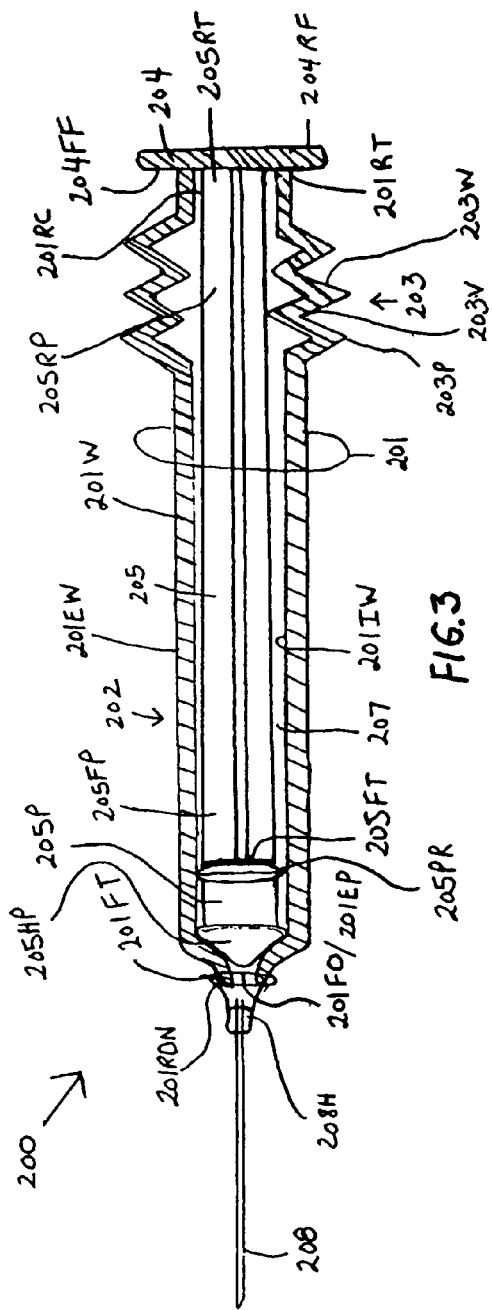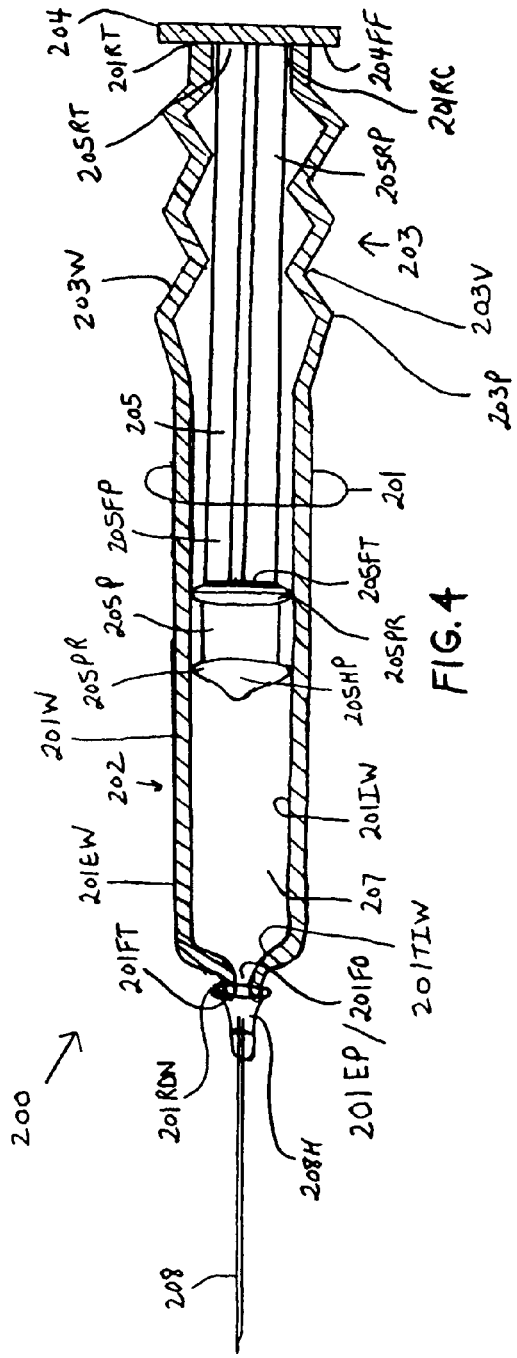
FIG. 3
FIG. 4

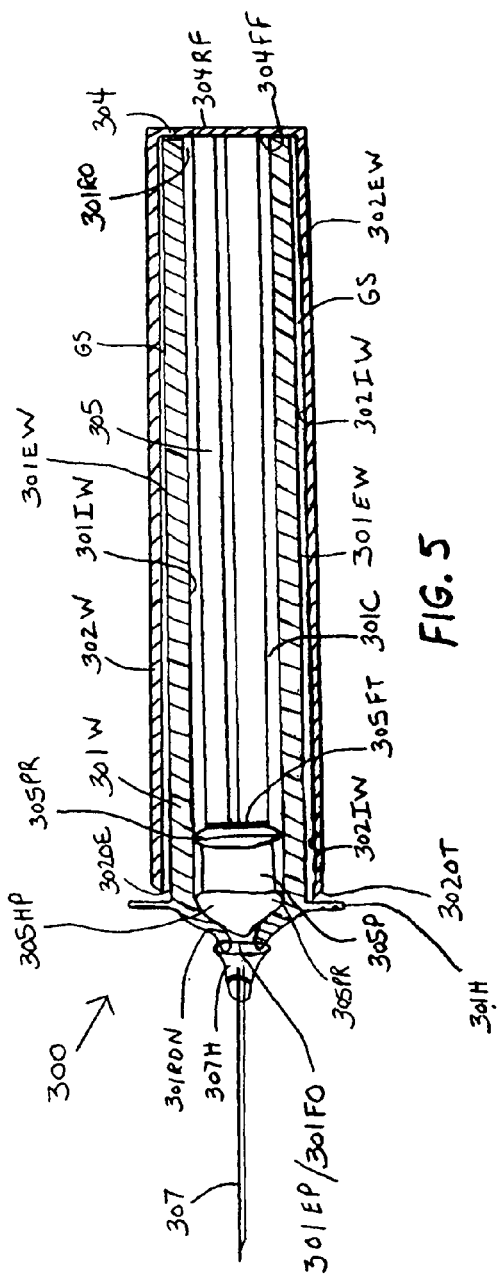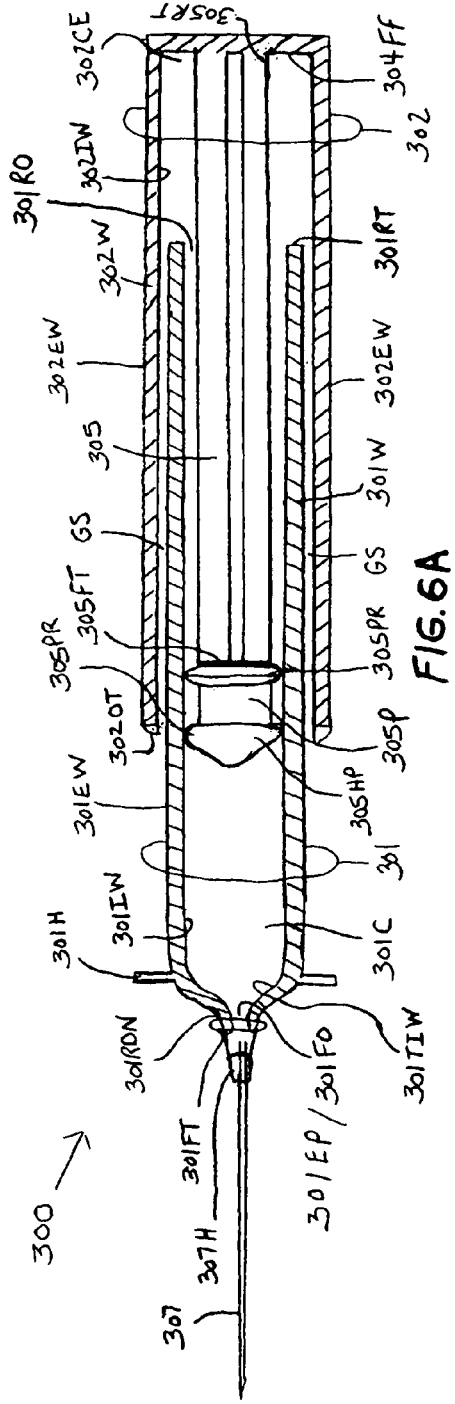

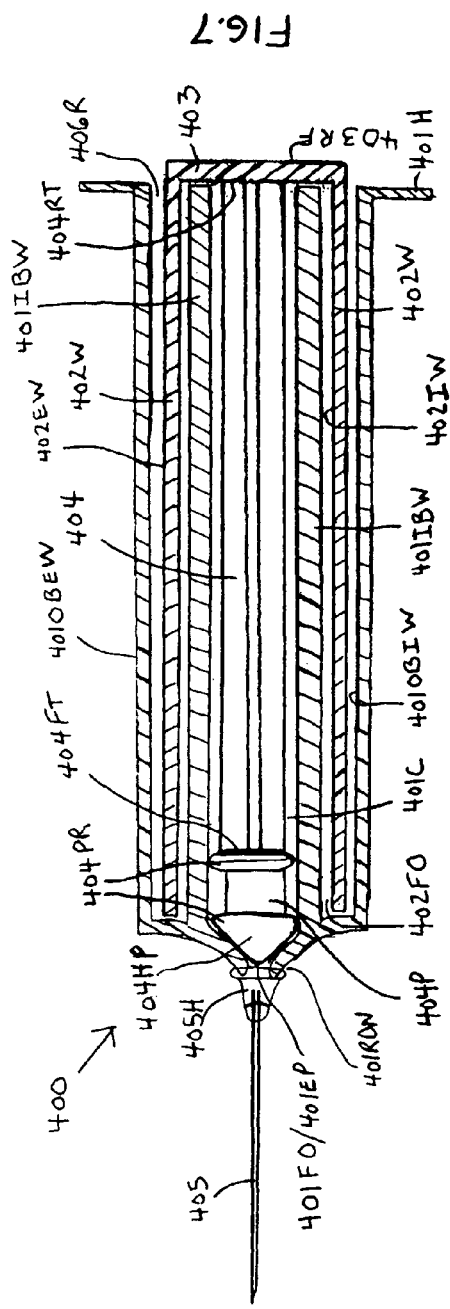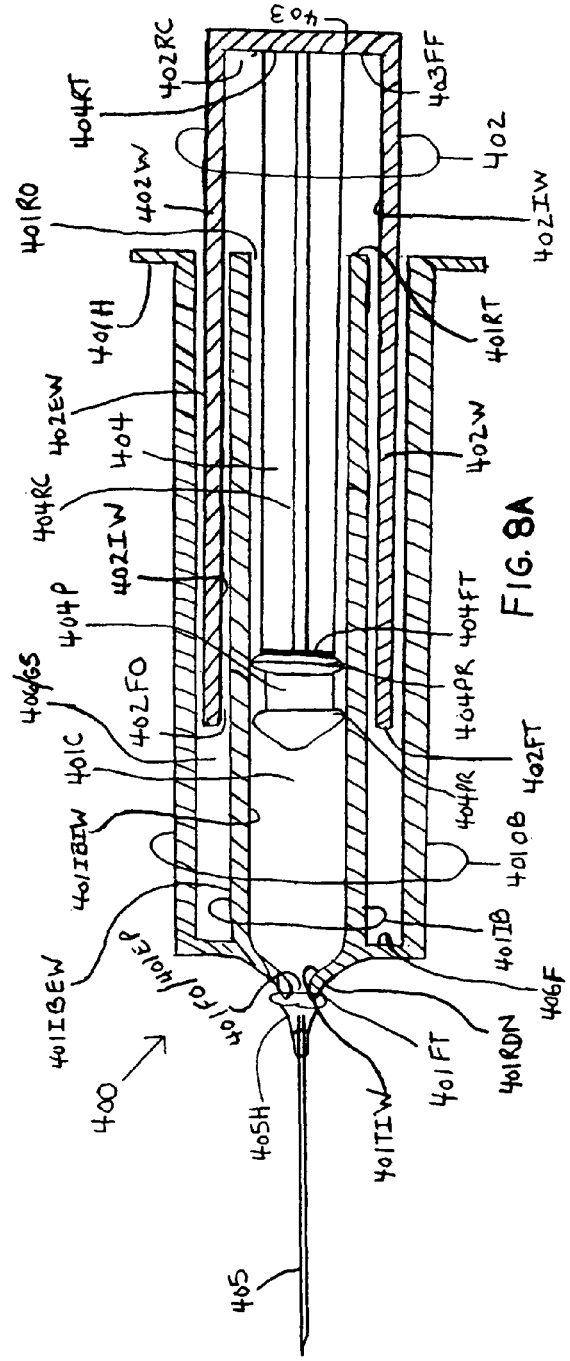

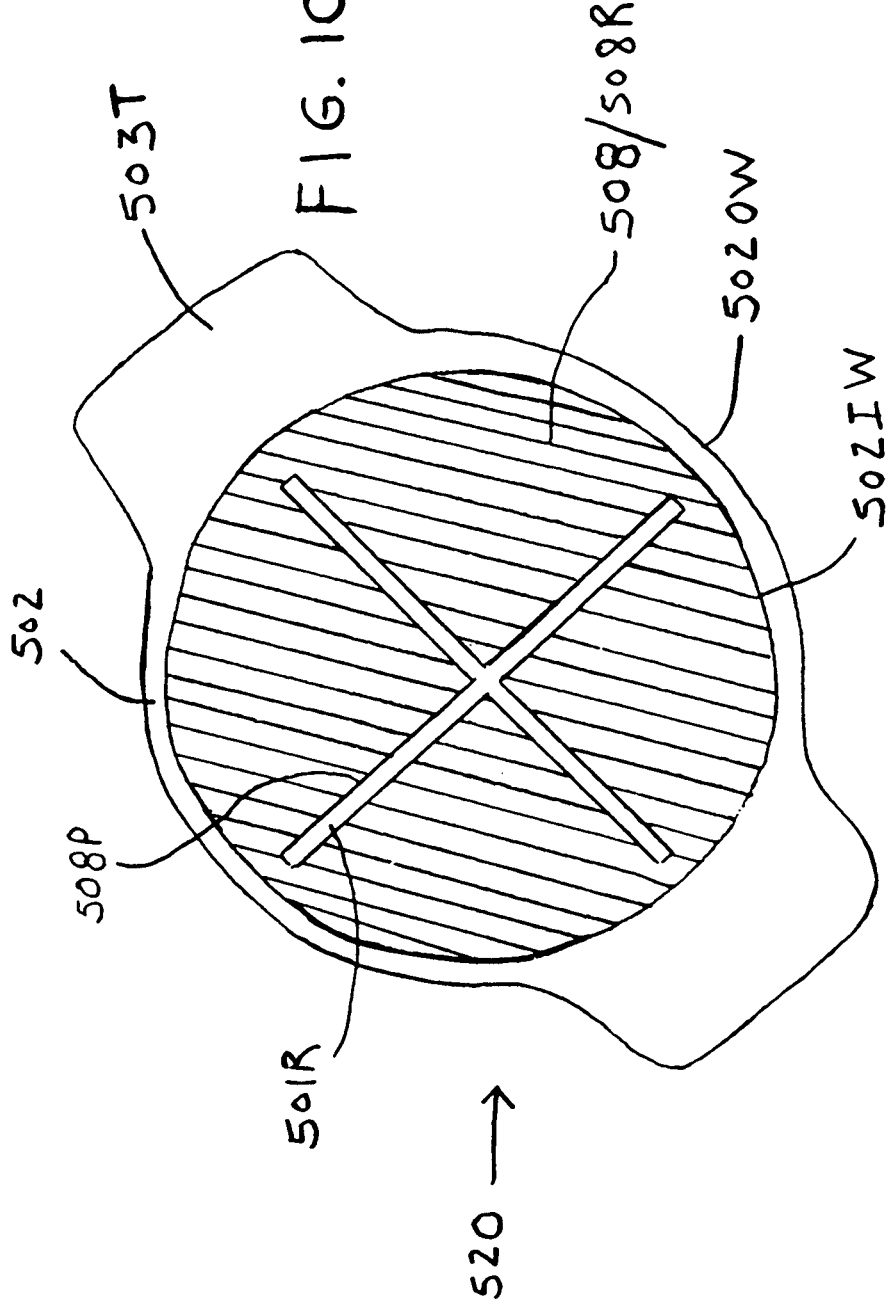

SYRINGE AND METHOD OF USING

This application is a Divisional of U.S. application Ser. No. 11/640,648 filed on Dec. 18, 2006, U.S. Pat. No. 7,842,017, which is a Divisional of U.S. application Ser. No. 10/949,016 filed on Sep. 24, 2004, U.S. Pat. No. 7,175,609 which is a divisional of U.S. application Ser. No. 10/057,519 filed on Jan. 24, 2002, U.S. Pat. No. 6,830,564 B2.

BACKGROUND OF THE INVENTION

Syringes are used by medical personnel to withdraw blood from patients, inject intravenous medications into patients, inject intramuscular medications into patients, prepare irrigation solutions, prepare dialysis fluids, prepare intravenous pushes, prepare bolus fluids, prepare intravenous fluids for parenteral injection, and prepare oral dose medications. Personnel trained to prepare solutions, pushes, or other fluids for injection prepare the solutions within a laminar flow hood or a vertical flow hood using aseptic technique. The hood provides a work area which reduces the probability of contaminants being introduced into the intravenous admixtures or other solutions during their preparation. Vertical flow hoods and biohazard hoods additionally reduce the probability of escape of biohazard materials being used from the work area and hood. The intravenous fluids, admixtures, and other solutions are prepared by placing a bag or bottle of fluid for injection, along with a needle, syringe, and the injectable medication, into the delineated work area in the hood. The medication is drawn from an ampoule or vial, for example, into the syringe using a needle and is then injected into the bag of intravenous fluid for injection. The fluid for injection can be a push bag, minibag, large volume parenteral, lipids or fat emulsion, etc. The bag or bottle of fluid for injection, apart from its therapeutic value, functions as a vehicle for delivering the medication, electrolytes, or other additives to the patient intravenously.

The individuals preparing the intravenous solutions are typically gowned, gloved, and use aseptic technique during the course of preparing the intravenous fluids. When preparing solutions for injection, it is necessary for the individual preparing the intravenous fluids to move their hands in and out of the laminar flow work area and also out of the laminar flow hood. Accordingly, while the hands are outside the work area and the hood, contaminants in the outside environment are introduced onto the hands or gloves of the individual preparing the intravenous solutions. In addition, the outer packaging used to hold the intravenous additives, ampoules, vials, syringes, needles, and other items used in preparing the solutions is not sterile and can carry contaminants which can be transferred or deposited onto the hands and fingers or gloves of the individual preparing the intravenous admixtures. While aseptic technique is used by the personnel preparing the solutions to reduce the tendency of introducing contaminants into the solutions being prepared, these contaminants can gain entry into the medication that has been drawn-up into the syringe barrel by their being deposited onto the inside surfaces of the syringe barrel by way of the barrel opening and/or plunger. Although not encouraged, inadvertent contact of the plunger shaft typically occurs with the hands, fingers, or gloves during the preparation of a solution. If the air, hands, fingers, or gloves are carrying contaminants such as dirt, lint, viruses, bacteria, microorganisms, dust, germs, pathogens, paper fibers, etc., then these contaminants can be deposited onto the plunger shaft surface and/or fall into the rearward barrel opening and subsequently be deposited onto the inner barrel walls. While a handle portion is usually located on the rearward end portion of the plunger to aid an individual in sliding the plunger into and out of the syringe barrel, larger syringes are typically difficult to handle using only one hand, or even both hands, because of the syringe size, plunger length, and friction created by surface area contact between the internal wall surfaces of the syringe barrel and the plunger piston surface. As a result, the plunger is often grasped by its shaft to gain leverage for aiding the individual preparing the intravenous fluids in pulling the plunger and piston along the hollow or cavity of the inner syringe barrel length to draw medication into the syringe cavity. Because the barrel end is open, grasping the plunger shaft allows contaminants present on the hands, fingers, or gloves to be deposited on the plunger shaft. These contaminants may also fall into the rearward end opening of the syringe barrel and contact the inner surfaces of the syringe barrel. The outside surfaces of the piston and the medication in contact with the inside syringe barrel surfaces can pick up these contaminants and ultimately deliver them to the solutions being prepared. Syringes and plungers currently in use do little to discourage the introduction of contaminants onto the plunger shaft and inner syringe barrel surface. The current syringes also suffer from problems of piston failure or detachment of the piston from the forward end of the plunger shaft causing loss of the seal between the piston and the inner surfaces of the syringe barrel. When this occurs, medication in the syringe barrel leaks or flows out of the syringe barrel rearward end opening and onto the hands, fingers, gloves, and work surface. When the material is blood or the medication or additive being used to prepare the solutions is a biohazard material such as certain chemotherapy drugs, acids, or radioactive pharmaceuticals, the safety of the individual working with the material is compromised because of exposure to and contact with the hazardous material.

On occasion, nurses or other personnel are required to prepare intravenous admixtures because of a patient's immediate requirement for a medication. These admixtures are prepared in non-sterile environments and generally without the use of aseptic technique. The syringes of the instant invention provide an added level of protection to the medication when working in a non-sterile environment.

An additional problem which plagues current syringe designs is the problem resulting from pulling the forward end of the plunger and piston to close to the rearward end opening of the syringe barrel cavity leading to accidental separation of the plunger from the barrel. Also, when the piston and forward end of the plunger are withdrawn along the syringe barrel cavity and positioned close to the rearward syringe barrel opening, the plunger shaft and medication in the syringe cavity is in increased jeopardy of contamination. Additionally, any rocking motion caused to the plunger shaft while in this position tends to compromise the seal between the piston and the syringe barrel inner surface causing leaking of the medication.

The instant invention overcomes the drawbacks noted above.

SUMMARY OF THE INVENTION

This invention relates to a new and improved syringe for use in withdrawing blood from patients, injecting intravenous medications into patients, preparing pre-filled syringes with medications for injection, preparing irrigation solutions, preparing dialysis fluids, preparing intravenous pushes, preparing bolus fluids, preparing intravenous fluids, preparing large volume parenterals for intravenous injection, preparing oral dose medications, and preparing medications requiring chemotherapy drugs, acids, or radioactive pharmaceuticals, etc.

In a first embodiment of this invention, it is an object to provide a new and improved syringe having a corrugated sheath, cover, or shield concentrically enveloping a plunger shaft. The forward end terminus of the corrugated sheath, cover, or shield is attached or molded to the rearward end face surface of the syringe barrel handle member which is formed, or molded, on the rearward end terminus of the syringe barrel. The rearward end terminus of the corrugated sheath, cover, or shield is attached by molding, fusing, adhesives, ultrasonic bonding or welding, thermal bonding, etc., to the forward face surface of a plunger handle member which is also centrally molded, or formed on the rearward end terminus of the plunger shaft. The rearward end terminus of the plunger shaft is centrally molded to the forward face surface of the plunger handle member with the forward end and body of the plunger shaft extending and movably fitted into the cavity, fluid reservoir, or hollow portion of the syringe barrel. The syringe barrel is formed with two open ends at opposite ends of the syringe bore or cavity—one end having a larger diameter opening than the opposite end. The larger diameter opening is located at the rearward end terminus of the syringe barrel. The smaller diameter opening is located at the forward end terminus of the syringe barrel and has a reduced diameter neck at the entrance/exit port. The corrugated sheath, cover, or shield encloses and surrounds the rearward end portion of the plunger shaft extending between the syringe barrel handle member and the plunger handle member. The sheath encloses and surrounds that portion of the longitudinal axis of the plunger shaft located and housed within the central cavity or hollow of the corrugated sheath and between the barrel handle and plunger shaft handle when the corrugated sheath is in a compressed state and in a lengthened state. Thus, the plunger shaft and rearward end syringe barrel opening are closed off from and not exposed to the outside environment. The plunger shaft is withdrawn from the syringe barrel cavity or hollow by grasping the syringe barrel outer surface with one hand and the plunger shaft handle member and/or corrugated sheath outer surface with the other hand and pulling the plunger shaft handle member and/or corrugated sheath such that the plunger shaft emerges from the hollow or cavity of the syringe barrel through the rearward end opening of the syringe barrel. The peaks and walls of the corrugations, pleats, or folds in the sheath are caused to separate along the longitudinal axis of the sheath thereby lengthening the sheath along its longitudinal axis. The plunger shaft remains centrally located within the hollow of the corrugated sheath as the plunger shaft emerges from the cavity and rearward end opening of the syringe barrel. As the corrugations or folds in the sheath separate, the corrugated sheath lengthens enabling the plunger shaft to be withdrawn from the hollow or cavity of the syringe barrel. The corrugated sheath lengthens concentrically around and along the plunger shaft. That is, the corrugated sheath lengthens and encloses a greater length of the plunger shaft as the plunger shaft is further withdrawn from the syringe barrel hollow. The sheath remains in the lengthened or elongated position until a force is applied longitudinally to the plunger shaft to compress or collapse the folds or corrugations of the sheath together. That is, it is not necessary for an individual to hold the withdrawn plunger or lengthened corrugated sheath such that it remains in its lengthened state. The corrugated sheath is designed and manufactured such that it does not automatically recoil. A force must be applied along the longitudinal axis of the syringe plunger shaft and corrugated sheath to cause the ends of the elongated corrugated walls of the sheath to be moved toward each other such that the corrugated sheath shortens. When the walls of the corrugated sheath are forced together, the sheath shortens. Shortening of the corrugated sheath is performed by pressing or applying a force to the plunger member such that the forward end face surface of the plunger handle member advances toward the rearward end opening of the syringe barrel to cause the sheath to shorten and the plunger shaft and piston to slide along the longitudinal axis of the syringe barrel cavity toward the syringe entrance/exit port such that medication in the syringe barrel cavity is ejected from the syringe through the entrance/exit port. The piston rim slidably engages and maintains a tight seal with the internal wall surfaces of the syringe barrel cavity as the piston advances. The liquid medication in the cavity remains forward of the piston head during advancement of the plunger and piston such that the medication in the syringe barrel cavity is ejected from the syringe cavity through the entrance/exit port or forward end opening. An advantage of using the corrugated sheath is the protection provided by the sheath to the plunger shaft and the internal cavity wall surfaces in that contaminants deposited onto the external wall surfaces of the corrugated sheath or syringe barrel will not jeopardize the sterility of the inner cavity of the syringe barrel because the contaminants cannot penetrate the corrugated sheath or syringe barrel. Additionally, the corrugated sheath is designed to elongate only to a length that enables the piston rim to be aligned with the maximum increment reading on the syringe barrel wall which functions to prevent separation of the plunger from the rearward end opening of the syringe barrel.

In a second embodiment of the instant invention, it is an object to provide a new and improved syringe having a corrugated barrel. The syringe barrel has a straight segment and a corrugated segment. The corrugations are molded into the syringe barrel to form the corrugated segment at a point on the barrel that is greater than the maximum volume increment reading on the straight segment of the syringe barrel. Thus, the syringe barrel has a straight segment and a corrugated segment. The straight segment is located on the forward end of the syringe barrel and the corrugated segment is located at the rearward end of the syringe barrel. The straight segment and the corrugated segment are continuous with each other. A plunger handle member is molded to rearward end of the syringe barrel at the terminus of the syringe barrel corrugated segment. The rearward end terminus of the plunger shaft is centrally molded to the forward face surface of the plunger handle member. A rearward portion of the plunger shaft body is enclosed or surrounded by the corrugated segment of the syringe barrel. The syringe barrel is formed with an open end and a closed end. The closed end is closed by the plunger handle member which is molded to the rearward end of the syringe barrel at the terminus of the syringe barrel corrugated segment. The open end is located at the forward end terminus of the syringe barrel and has a reduced diameter neck at the entrance/exit port. A forward end portion of the plunger shaft body and a piston located at the forward end terminus of the plunger shaft is movably fitted into and enclosed or surrounded by the straight segment of the syringe barrel. The piston and plunger shaft body are caused to traverse the longitudinal axis of the syringe barrel cavity, fluid reservoir, or hollow by grasping the outer syringe barrel surface with one hand and the plunger shaft handle member and/or external walls of the corrugated segment with the other hand and pulling the plunger shaft handle member and/or corrugated segment such that the forward face surface of the plunger handle member moves away from the straight segment of the syringe barrel causing lengthening of the syringe barrel and elongation of the corrugated segment. Simultaneously, the plunger piston mounted or attached by fusing, molding, adhesives, ultrasonic bonding or welding, thermal bonding, etc., to the forward end terminus of the plunger shaft slidably engages the internal wall surfaces of the straight segment of the syringe barrel as the piston longitudinally traverses the cavity or hollow of the syringe barrel. In order to assist the user in lengthening of the syringe by pulling the plunger shaft handle member, a syringe barrel handle member can be molded to the external circumferential wall surface of the syringe barrel on the straight segment of the syringe barrel at a desired location. The syringe barrel handle member can be used as a wall for leverage to assist the user in lengthening or shortening the syringe barrel while pulling or pushing the plunger shaft handle. The peaks and walls of the corrugations or folds in the corrugated segment of the syringe barrel are caused to separate or spread apart along the longitudinal axis of the syringe barrel as the plunger handle member is pulled thereby lengthening the syringe barrel along its longitudinal axis. At least a portion of the plunger shaft remains centrally located within, and the walls of the piston rim remain in contact with, the internal walls of the hollow or cavity of the syringe barrel straight segment during elongation or lengthening of the syringe barrel. The rearward end terminus of the plunger shaft and the corrugated segment rearward end terminus remain molded to the forward end face surface of the plunger handle member. As the corrugations or folds of the corrugated segment separate or spread apart, the corrugated segment of the syringe barrel lengthens causing the body of the plunger shaft and piston to slide along the straight segment of the syringe barrel cavity in the direction of the corrugated segment and away from the forward end of the syringe barrel. The piston rim is in contact with and forms a seal with the internal cavity walls of the syringe barrel. The corrugated segment encloses or houses and surrounds or encircles a greater length of the plunger shaft body as the plunger shaft and piston are drawn further along the syringe barrel hollow straight segment toward the corrugated segment. Once lengthened, the folds or corrugations of the corrugated segment remain in the lengthened and separated or spread apart position until a force is used to compress or collapse together the folds or corrugations of the corrugated segment. That is, it is not necessary for the individual pulling the plunger handle member and lengthening the corrugated segment to hold the plunger handle member or corrugated segment such that the corrugated segment remains in its lengthened position. The corrugated segment is designed and manufactured such that it does not automatically recoil. This design avoids automatic recoil action and maintains the corrugated segment in the desired lengthened position when drawing medications or other fluids into the syringe barrel. An automatic recoil would force the fluids out of the syringe barrel. An axial force must be applied to the syringe barrel along its longitudinal axis to cause the elongated corrugated segment walls to move toward each other such that the syringe barrel shortens along its longitudinal axis. When the walls of the corrugated segment are forced together, the syringe barrel shortens. Shortening of the corrugated segment can be performed by pressing against the rearward face surface of the plunger shaft handle member in a direction along the axial length of the syringe barrel to cause the corrugated segment to shorten and the plunger piston to slide along the internal side wall surfaces of the syringe barrel cavity toward the forward end and syringe entrance/exit port such that the medication in the syringe barrel cavity is ejected from the syringe through the entrance/exit port. Note that the plunger shaft remains housed within the syringe barrel during operation and non-operation. An advantage of using the straight segment and corrugated segment syringe barrel is the protection provided to the plunger shaft and the internal cavity wall surfaces in that contaminants deposited onto the external wall surfaces of the straight and corrugated segments of the syringe barrel will not jeopardize the sterility of the inner cavity of the syringe barrel because the contaminants cannot penetrate the closed walls of the syringe barrel. Additionally, the corrugated segment is designed to elongate to a length that enables the piston rim to substantially align with the maximum increment reading indicia formed on the syringe barrel straight segment. Because the rearward end terminus of the syringe barrel, at the terminus of the corrugated segment, is molded to the forward face surface of the plunger handle member, and the forward face surface of the plunger handle member is also molded to the rearward end terminus of the plunger shaft, separation of the plunger from the syringe barrel is prevented.

In a third embodiment of the instant invention, it is an object to provide a new and improved syringe having mating concentric plunger member and syringe barrel walls. The plunger member has a cylindrical wall having an open end and a closed end. The closed end of the plunger member has a flat bottom floor structure that forms a hollow cup shape with the plunger member cylindrical walls. It is noted that other shapes other than a flat shape can be provided to the bottom floor structure. The flat bottom floor structure has forward and rearward face surfaces. The flat bottom floor structure can be molded continuous with the plunger member cylindrical walls. The inside diameter of the plunger member is constant along its length. The forward face surface of the flat bottom floor structure has centrally molded thereto the terminus end of a plunger shaft. The plunger shaft is concentrically surrounded by the internal wall surfaces of the plunger member along its longitudinal length. The plunger shaft extends normal from the forward face surface of the flat bottom floor structure along the length of the internal wall surfaces of the plunger member which concentrically surround and enclose or house the plunger shaft. The plunger shaft has a piston mounted, fused, molded, or attached to its forward end terminus. The rim of the piston coincides with the terminus of the plunger member walls at their open end. The syringe barrel is formed with two open ends at opposite ends of the syringe bore or cavity—one end having a larger diameter opening than the opposite end. The larger diameter opening is located at the rearward end terminus of the syringe barrel. The smaller diameter opening is located at the forward end terminus of the syringe barrel and has a reduced diameter neck at the entrance/exit port. The syringe barrel has an outside wall diameter less than the inside wall diameter of the plunger member along its entire length. The inside diameter of the syringe barrel is slightly less than the diameter of the rim portion of the piston. The piston is attached to the forward end terminus of the plunger shaft by mounting, fusing, molding, adhesives, ultrasonic bonding or welding, thermal bonding, etc, such that a tight seal is formed therebetween. The rim portion of the plunger piston mates with and forms a seal with the internal wall surfaces of the bore or cavity of the syringe barrel. The internal and external wall surfaces of the syringe barrel taper at its forward end forming the reduced diameter neck having the smaller diameter opening and an entrance/exit port through which fluid medications and/or other solutions enter and exit the cavity of the syringe barrel. The external wall surface of the reduced diameter neck forms a mating surface for the hub of a needle. At a point rearward of the reduced diameter neck and forward end opening of the syringe barrel, a handle member can be provided on the external syringe barrel wall for assisting the user in sliding of the plunger member relative to the syringe barrel.

The plunger member is mated with the syringe barrel by movably fitting the plunger piston located at the forward end terminus of the plunger shaft into the central cavity, fluid reservoir, or bore of the syringe barrel. As the piston and plunger shaft are slid into the central cavity of the syringe barrel, the internal wall surfaces of the plunger member form a face-to-face relationship with the external wall surfaces of the syringe barrel. The plunger shaft and piston slide into the full length of the central cavity of the syringe barrel such that the head of the piston abuts the tapered internal forward end walls of the syringe barrel. The contour of the head of the piston matches and follows the contours of the tapered internal walls of the syringe barrel to form a seal at the passageway of the entrance/exit port. The terminus surfaces of the larger diameter opening of the syringe barrel can abut with the inner face surface of the flat bottom floor structure of the plunger member. In operation the walls of the outer plunger member walls concentrically surround the syringe barrel walls. In operation, medication is drawn up from a vial or ampoule, for example, by first introducing the needle attached to the external walls of the reduced diameter neck into the vial containing the medication. Next, the internal wall surface of the plunger member is concentrically slid alongside the length of the external wall surface of the syringe barrel while maintaining a concentric glide space between the internal wall surface of the plunger member and the external wall surface of the syringe barrel. Simultaneously, as the plunger member wall is slid along the length of the syringe barrel wall, the piston attached at the forward end terminus of the plunger shaft slidably engages and maintains a tight seal with the internal wall surfaces of the syringe barrel cavity while moving along the syringe barrel cavity and away from the internal tapered walls of the syringe barrel. This causes the air column in the bore or cavity located behind the piston and along the plunger shaft to be expelled or pushed out of the cavity creating a vacuum in the space located between the forward end of the piston head and the internal tapered wall surfaces of the syringe barrel. The vacuum causes the liquid medication in the vial or ampoule to be drawn into the syringe barrel cavity through the needle and the entrance/exit port passageway. The needle is then removed from the medication vial or ampoule and positioned in the needle port of an appropriate bag or bottle of intravenous solution, for example. The liquid medication can then be injected into the bag or bottle of intravenous solution by applying pressure to the rearward face surface of the flat bottom floor structure. This pressure causes the longitudinal length of the plunger shaft and the plunger piston to advance along the cavity of the syringe toward the tapered internal wall surfaces of the syringe cavity. The piston rim slidably engages and maintains a tight seal with the internal wall surfaces of the syringe cavity as the piston advances. The liquid medication remains forward of the piston head during advancement of the plunger and piston. The liquid medication is ejected out of the entrance/exit port of the syringe barrel as the plunger is advanced. An advantage of using the syringe having mating concentric plunger and syringe barrel walls is the protection provided to the plunger shaft and the internal cavity wall surfaces of the syringe barrel in that contaminants deposited onto the external wall surfaces of the plunger member or syringe barrel will not jeopardize the sterility of the inner cavity of the syringe barrel because the design discourages entry of contaminants into the syringe barrel cavity.

An added feature for the third embodiment is to provide a first sealing ring to the inner wall surface of the plunger member at or near its open end terminus. A second sealing ring is formed on the external wall surface of the syringe barrel at or near its large diameter terminus. The sealing rings traverse the entire circumference or perimeter of the surface to which they are formed. The sealing rings are preferably formed of a flexible material and extend from their surface origin a distance less than or equal to the distance to the opposing surface. The sealing rings can have any desired cross-sectional shape such as triangular, square, circular, etc. The sealing rings provide several benefits and advantages. First, the sealing rings seal the glide space existing between the internal wall surface of the plunger member and the external wall surface of the syringe barrel. This discourages entry of contaminants such as dirt, dust, microorganisms, and pathogens, and any other type of contaminant carried by the air, hands, fingers, gloves, etc., that may become deposited onto the external surfaces of the syringe barrel from entering the syringe and becoming deposited on the internal walls of the syringe cavity or in the medication in the syringe barrel. Second, the sealing rings function to prevent accidental separation of the plunger member from the syringe barrel through abutment of the sealing rings as the walls of the plunger are moved relative to the walls of the syringe barrel. Third, the sealing rings function as a dam or barrier to medications or other fluids that leak from the syringe cavity and collect or accumulate in the cup of the plunger member due to piston failure.

In a fourth embodiment of the instant invention, it is an object to provide a new and improved syringe having concentric syringe barrels and a plunger member. The plunger member has a wall having an open end and a closed end. The closed end of the plunger member has a flat bottom floor structure that forms a hollow cup shape with the plunger member cylindrical walls. It is noted that other shapes other than a flat shape can be provided to the bottom floor structure. The flat bottom floor structure has forward end and rearward end face surfaces. The flat bottom floor structure can be molded continuous with the walls of the plunger member. The inside diameter of the plunger member walls is constant along their length. The forward end face surface of the flat bottom floor structure has centrally molded thereto the terminus end of a plunger shaft. The plunger shaft can also be molded continuous with the flat bottom floor structure. The plunger shaft is centrally located within and surrounded by the internal wall surfaces of the plunger member. The plunger shaft extends centrally and normal from the forward face surface of the flat bottom floor structure along the length of the plunger member walls. The walls of the plunger member extend normal from the plane of the forward end face surface of the flat bottom floor structure and concentrically surround the plunger shaft. The plunger shaft has a piston attached by mounting, fusing, molding, adhesives, ultrasonic bonding or welding, thermal bonding, etc to its forward end terminus. The rim of the plunger piston coincides with the terminus of the walls of the plunger member at its open end. The concentric syringe barrel is formed with inner and outer syringe barrels. An inner concentric syringe barrel is formed with two open ends located at opposite ends of the inner concentric syringe barrel cavity—one end having a larger diameter opening than the opposite end. The larger diameter opening is located at the rearward end terminus of the inner concentric syringe barrel. The smaller diameter opening is located at the forward end terminus of the concentric syringe barrel and has a reduced diameter neck at the entrance/exit port. The inner syringe barrel has an outside diameter less than the inside diameter of the plunger member walls along the entire length of the inner syringe barrel. The inside diameter of the inner syringe barrel is slightly less than the diameter of the rim portion of the plunger piston which is attached by mounting, fusing, molding, adhesives, ultrasonic bonding or welding, thermal bonding, etc., to the forward end terminus of the plunger shaft. The rim portion of the plunger piston mates with and forms a seal with the internal wall surfaces of the bore or cavity of the inner syringe barrel. The internal and external wall surfaces of the inner syringe barrel taper at their forward ends forming the reduced diameter neck having the smaller diameter opening and an entrance/exit port through which fluid medications and other solutions or fluids enter and exit the cavity of the inner syringe barrel. The external wall surface of the reduced diameter neck forms a mating surface for the hub of a needle. An outer syringe barrel concentrically encircles the inner syringe barrel forming concentric syringe barrels. The internal wall surfaces of the outer syringe barrel are in face-to-face relationship with the external wall surfaces of the inner syringe barrel and are separated by a distance which forms a second cavity or space between the inner syringe barrel wall and the outer syringe barrel wall. This second cavity or space is open at its rearward end and closed at its forward end forming a cup shape. The open end receives the walls of the plunger member. This second cavity or space functions as a glide space for the walls of the plunger member. At a point located at the terminus of the opening on the external wall surface of the outer syringe barrel, a handle member can be provided for assisting the user in sliding the plunger member relative to the inner and outer syringe barrels.

The plunger member is mated with the concentric syringe barrel member by movably fitting the plunger piston, located at the forward end terminus of the plunger shaft, into the central cavity, fluid reservoir, or bore formed by the inner syringe barrel walls. As the piston and plunger shaft are slid into the central cavity of the inner syringe barrel, the internal wall surfaces of the plunger member form a face-to-face relationship with the external wall surfaces of the inner syringe barrel. Also, the external wall surfaces of the plunger member form a face-to-face relationship with the internal wall surfaces of the outer syringe barrel. The plunger shaft and piston slide into the full length of the central cavity of the inner syringe barrel such that the head of the piston abuts the tapered internal walls of the inner syringe barrel. The contour of the head of the piston matches and follows the contours of the tapered internal walls of the inner syringe barrel to form a seal at the passageway of the entrance/exit port. The terminus surfaces of the larger diameter opening of the inner syringe barrel can abut with the inner face surface of the flat bottom floor structure of the plunger member. In operation, the walls of the concentric syringe barrels concentrically surround the plunger member walls. Medication is drawn up from a vial or ampoule, for example, by first introducing the needle, attached to the external walls of the reduced diameter neck of the entrance/exit port, into the vial or ampoule containing the medication. Next, the longitudinal wall surfaces of the plunger member are concentrically slid within the glide space existing between and along the length of the external wall surface of the inner syringe barrel and the internal wall surface of the outer syringe barrel. Simultaneously, as the plunger member wall is slid within the glide space along the length of the external wall surface of the inner syringe barrel and the inner wall surface of the outer syringe barrel, the piston attached at the forward end terminus of the plunger shaft slidably engages and maintains a tight seal with the internal wall surfaces of the inner syringe barrel cavity while moving along the inner syringe barrel cavity and away from the internal tapered walls of the inner syringe barrel. This causes the air column in the bore or cavity located behind the piston and along the plunger shaft to be pushed out of the cavity creating a vacuum in the space located between the forward end of the piston head and the tapered internal wall surfaces of the inner syringe barrel. The vacuum causes the liquid medication in the vial or ampoule to be drawn into the inner syringe barrel cavity through the needle and the entrance/exit port passageway. The needle is then removed from the medication vial or ampoule and positioned in the needle port of an appropriate bag or bottle of intravenous solution. The liquid medication can then be injected into the bag or bottle of intravenous solution by applying pressure to the rearward face surface of the flat bottom floor structure. This pressure causes the longitudinal length of the plunger shaft and the plunger piston to advance along the cavity of the inner barrel of the syringe toward the tapered internal wall surfaces of the inner barrel syringe cavity. The piston rim slidably engages and maintains a tight seal with the internal wall surfaces of the inner syringe barrel cavity as the piston advances. The liquid medication remains forward of the piston head during advancement of the plunger and piston. The liquid medication is ejected out of the entrance/exit port of the syringe cavity of the inner barrel as the plunger is advanced. An advantage of using a syringe having concentric inner and outer syringe barrels which mate concentrically with a plunger member is the protection provided to the plunger shaft and the internal cavity wall surfaces of the syringe in that contaminants deposited onto the external wall surfaces of the plunger member or syringe barrel will not jeopardize the sterility of the cavity of the inner syringe barrel because the design discourages entry of contaminants into the inner syringe barrel cavity.

An added feature for the fourth embodiment is to provide a first sealing ring to the internal wall surface of the outer syringe barrel at or near its open-end terminus. A second sealing ring can be formed on the external wall surface of the plunger member at or near the terminus of its open end. A third sealing ring can be formed on the internal wall surface of the plunger member at or near the terminus of its open end. Fourth and fifth sealing rings can be formed on the internal and external surfaces of the inner syringe barrel at or near the terminus of its open end. One or more of the above sealing rings can be formed or provided on the wall surfaces of the concentric syringe or plunger member. The sealing rings traverse the entire circumference or perimeter of the surface to which they are formed. The sealing rings provide several advantages. The sealing rings are preferably formed of a flexible material and extend from their surface origin a distance less than or equal to the distance to the opposing surface. The sealing rings can have any desired cross-sectional shape such as triangular, square, circular, etc. The sealing rings provide several benefits. First the sealing rings function as a barrier by sealing the glide space existing between the internal wall surface of the outer syringe barrel and the external wall surface of the inner syringe barrel. This discourages entry of contaminants such as dirt, microorganisms, dust, pathogens, and other types of contaminants, carried by air, hands, fingers, gloves, etc., which may become deposited onto the internal surfaces of the inner syringe barrel cavity. Second, the sealing rings function to prevent separation of the plunger member from the concentric syringe barrels through abutment of the sealing rings on the syringe barrels with the sealing rings of the plunger member as the walls of the plunger member are moved relative to the walls of the inner and outer concentric syringe barrels. Third, the sealing rings function as a dam or barrier to fluids that leak from the syringe barrel cavity and collect or accumulate in the cup of the plunger member due to piston failure.

In a fifth embodiment of the instant invention, it is an object to provide a new and improved syringe having a contaminant shield positioned at the rearward end opening of the syringe barrel. The contaminant shield is formed on the rearward end syringe barrel inner wall surface using a semi-rigid and flexible material. The contaminant shield projects perpendicularly from the circumference or perimeter of the syringe barrel inner wall surfaces into the syringe barrel cavity and surrounds and abuts the surfaces and walls of the ribs which form the spine of the plunger shaft. The contaminant shield can be formed from a single material or a mixture of materials which will provide a semi-rigid and flexible characteristic to the shield. To facilitate attachment of the contaminant shield to the inner wall surface of the syringe barrel cavity, a dovetail groove, or similar locking groove, can be formed in the surface of the syringe barrel inner wall along the circumference or perimeter at or near the rearward end opening of the syringe barrel. During the molding process, the dovetail groove receives and anchors the material used to form the contaminant shield. The contaminant shield has a forward end face surface facing the cavity of the syringe barrel and a rearward end face surface facing the plunger handle member.

Alternatively, the shield can be formed of two parts. The first part is formed of a material providing a rigid or hard characteristic or quality to the contaminant shield. The first part can be formed of the same material and molded continuous with the circumference of the inner wall surface of the syringe barrel at or near the rearward end opening of the syringe barrel. The first part, when formed, projects into the syringe barrel cavity perpendicularly from the circumference or perimeter of the inner wall surface of the syringe barrel. The first part has a forward face surface and a rearward face surface. The first part has centrally formed therethrough an opening having the shape of the cross-section of the plunger shaft used in conjunction with the syringe barrel. If the contaminant shield is formed separately, or with a different material than that used to form the syringe barrel cavity, then a dovetail groove, or similar locking groove, can be formed on the inner wall surface of the syringe barrel along the circumference or perimeter of the syringe barrel inner wall surface at or near the rearward end opening of the syringe barrel. During the molding process, the dovetail groove receives and anchors the material used to form the first part of the contaminant cover shield.

The second part of the contaminant shield is formed from a soft, flexible material that has a bendable characteristic. The second part is formed within the cross-sectional opening on the periphery of the first part. The second part projects from the periphery or edges of the first part and into the cross-sectional opening. The second part terminates as a flexible lip, edge, or periphery that defines the plunger shaft cross-sectional opening. During operation or use, the lip, edge, or periphery of the second part is in contact with the surfaces of the plunger shaft which fits within the cross-sectional opening and traverses the opening as the plunger shaft exits and enters the syringe barrel cavity. The second part is formed on the cross-sectional periphery of the first part. This can be accomplished by providing the external surface of the first part, at its edge or periphery, with a dovetailed shape, or other surface shapes such as slits or holes, which would provide a locking function to the cross-sectional periphery of the first part during its forming operation to which the second part can be formed about. Alternatively, a dovetailed groove or similar locking groove can be provided at and within the cross-sectional periphery or edge of the first part to receive and anchor the material used to form the second part of the contaminant shield. The rearward end terminus of the plunger shaft is centrally molded to the forward face surface of a plunger handle member with the body of the plunger shaft extending through the cross-sectional opening formed in the contaminant shield. The forward end terminus of the plunger shaft has a piston that is attached or formed thereto by mounting, fusing, molding, adhesives, ultrasonic bonding or welding, thermal bonding, etc, and, along with the plunger shaft, is movably fitted into the cavity, fluid reservoir, or hollow portion of the syringe barrel. The syringe barrel is formed with two open ends located at opposite ends of the syringe cavity. The rearward end of the syringe barrel has a plunger shaft cross-sectional opening as described above and the forward end terminus has a small diameter opening. The small diameter opening has a reduced diameter neck at the entrance/exit port. In operation, the plunger shaft is withdrawn from the syringe barrel cavity by grasping the outer syringe barrel surface with one hand and the plunger shaft handle member with the other hand and pulling the plunger shaft handle member such that the plunger shaft emerges from the hollow or cavity of the syringe barrel through the rearward end plunger shaft cross-sectional opening formed in the contaminant shield exposing the plunger shaft to the external environment. During withdrawal, the piston at the forward end terminus of the plunger shaft slidably engages and maintains a tight seal with the internal wall surfaces of the syringe barrel cavity while moving along the syringe barrel cavity and away from the internal tapered walls of the syringe barrel located at the forward end of the syringe barrel. This causes the air column in the bore or cavity behind the piston head and along the plunger shaft to be expelled or pushed out of the syringe cavity through the plunger shaft cross-sectional opening creating a vacuum in the space located between the forward end of the piston head and the internal tapered wall surfaces of the syringe barrel. The plunger shaft remains in a withdrawn position until a force is applied along the longitudinal axis of the plunger shaft in a direction toward the forward end terminus of the plunger shaft to cause the plunger shaft to pass through the plunger shaft cross-sectional opening formed in the contaminant shield and cause the plunger shaft and piston to advance along the longitudinal axis of the syringe barrel cavity toward the tapered internal wall surfaces and entrance/exit port of the syringe barrel. The inside diameter of the syringe barrel is slightly less than the diameter of the rim portion of the piston such that the piston rim slidably engages and maintains a tight seal with the internal wall surfaces of the syringe barrel cavity as the piston advances to maintain liquid medication or other fluid in the cavity forward of the piston head during advancement of the plunger and piston such that the medication or other liquid in the syringe barrel cavity is ejected from the syringe cavity through the entrance/exit port or forward end opening. As the plunger shaft and piston advance along the internal wall surfaces of the syringe barrel cavity, the semi-rigid flexible material or the flexible second part, depending on which contaminant shield design is used, contacts the surfaces of the plunger shaft while it is advanced through the plunger shaft cross-section of the contaminant shield providing a wiping and sweeping action to the surfaces of the plunger shaft in a direction away from the forward end terminus of the plunger shaft as the plunger shaft and piston are caused to traverse the syringe cavity toward the forward end terminus of the syringe barrel thereby aiding in preventing entry of contaminants into the syringe barrel cavity. The sweeping and wiping action functions to push contaminants such as dirt, dust, microorganisms, and pathogens, and any other type of contaminant carried by the air, hands, fingers, gloves, etc, that is subsequently deposited onto the exposed portion of the plunger shaft, in a direction away from the forward end of the plunger shaft and ultimately from entering the syringe barrel cavity by way of the plunger shaft. The contaminant shield also functions to prevent deposition of dirt, lint, viral components, bacteria, germs, dust, microorganisms, pathogens, paper fibers, and any other type of contaminant carried by the air, hands, fingers, gloves, etc., from falling into the rearward end opening of the syringe barrel and becoming deposited onto the internal surfaces of the syringe barrel cavity. The contaminant shield of the instant invention provides protection to the plunger shaft and the internal cavity wall surfaces of the syringe barrel in that contaminants deposited onto the outer surfaces of the contaminant covers will not jeopardize the sterility of the inner cavity of the syringe barrel holding the medication or other fluid because the contaminants cannot penetrate the walls of the contaminant guard or shield.

As an alternative to forming or molding the contaminant shield onto the inner wall surface of the syringe barrel, the contaminant shield can be formed separately from the syringe barrel and attached in a separate operation. For example, the contaminant shield could be formed with a wall extending perpendicularly from the forward face surface of the shield with the outer surface of the perpendicularly extending wall having grooves and/or threads formed thereon which mate with grooves and/or threads formed on the inner wall surfaces at the rearward end opening of the syringe barrel by screwing, turning, twisting, or rotating the threaded end cap contaminant shield into the grooved rearward end opening of the syringe barrel. Additionally, the shield portion of the end cap contaminant shield is formed with either the semi-rigid, flexible material or as the two-part material structure.

A further alternative includes providing a contaminant shield having walls extending perpendicularly from the forward face surface of the shield such that the outer surface of the perpendicularly extending walls have a flange or lip that mates with the inner wall surfaces of the syringe barrel at the rearward end opening through frictional fitting, snap fitting, locking, or a combination thereof.

Still further, the end cap contaminant shield can be manufactured as a flat or plate design without extending walls and having only the forward and rearward end face surfaces comprising first and second parts and an opening in the shape of the plunger shaft cross section. The forward face surface of the end cap contaminant shield is attached, bonded as by adhesives, ultrasonic bonding or welding, thermal bonding, etc., to the rearward end terminus of the syringe barrel. The plunger shaft functions and operates with the flat or plate end cap contaminant shield in the manner as previously described with the other end cap contaminant shield designs.

An advantage of using the shield is the protection provided by the shield to the internal cavity wall surfaces of the syringe in that contaminants deposited onto the rearward end wall surfaces of the shield will not jeopardize the sterility of the inner cavity of the syringe barrel because the contaminants are blocked by and cannot penetrate the shield.

An added function and benefit of the fifth embodiment is that the shield functions to prevent accidental separation of the plunger member from the syringe barrel by abutment of the forward face surface of the shield with forward end terminus of the plunger shaft or piston. Second, the shield functions as a temporary dam or barrier to fluids that may escape the syringe cavity due to piston failure. When the end cap contaminant shield is used, the forward end terminus of the end cap walls function to prevent accidental separation of the plunger member and syringe barrel by abutment of the forward end terminus of the end cap walls with the forward end terminus of the plunger shaft or piston.

The syringes and the components forming the syringes of the instant embodiments can be formed by injection molding, blow molding, extrusion, compression molding, or any other molding process or combination of molding processes that will accomplish the molding objective of forming the syringe components, such that the molded syringe components mechanically operate together to perform the desired function and achieve the desired results. The components used to form the syringes of the instant invention as set forth above in the foregoing embodiments can be formed of plastic materials, polymers, rubber materials, metals, alloys, glass materials, or combinations thereof. The materials used to mold the syringe components will depend on the capacity in which the syringe will be used and the type of solution or fluid with which the syringe will be used. That is, some materials are more stable and safer to work with or store when in glass syringes; while syringes formed with other materials is sufficient for working with other solutions or fluids. The syringe barrels should be substantially transparent so the solutions or fluids in the barrel cavity can be monitored with regard to the volume measuring indicia formed and depicted on the syringe barrel.

The syringes of the instant invention can be used for prepacking medications which will be used orally, for injection, for irrigations, for preparation of other solutions, etc. The syringes of the instant invention can also be used for manufacturing injectable or oral medications as pre-filled or pre-dosed syringes. The materials used to form the syringe components of the instant invention should be compatible with the ingredients of the pre-filled or pre-dosed medication, solution, other substances, etc., contained in the syringe during its storage so as to provide stability and a suitable shelf-life to the medication, solution, other substance, etc. Also, while shelved, the medications, solutions, other substances, etc., pre-filled and pre-dosed in the syringes of the instant invention should be protected in the syringes from adverse effects of moisture, atmospheric oxygen, and/or light when required.

In the case of single-dose, pre-dosed, or pre-filled syringes carrying an injectable or oral medication, a syringe of the instant invention can be manufactured, assembled, and filled with medication or other desired substance. The pre-filled syringe can be manufactured and assembled without a needle. A removable closure cap can be provided for the entrance/exit port at the reduced diameter neck. The user can remove the closure cap and attach a needle to the syringe when the medication is ready to use. Alternatively, the syringe of the instant invention can be manufactured and assembled with the needle as a unit wherein the needle or cannula can be permanently attached by molding, fusing, adhesives, ultrasonic bonding or welding, thermal bonding, etc., to the reduced neck at the forward end of the syringe barrel. A removable needle cap or sheath is provided and can be attached by a tamper-resistant means such that the needle cap or sheath houses or covers the needle and ensures the integrity of the contents of the syringe prior to use and during storage. Alternatively, the needle or cannula with needle cap or sheath can be removably attached to the reduced neck at the forward end of the syringe barrel by screwing, frictional fit, etc. Also, a tamper-resistant means can be provided with the removably attached needle or cannula and needle cap or sheath. The medication pre-filled or pre-dosed in the syringe of the instant invention by the manufacturer, with or without a needle, is packaged for use. The medication pre-filled or pre-dosed in the syringe of the instant invention by the manufacturer can be delivered to an individual as a single dose or as multiple doses. Because of the design of the syringes of the instant invention, the likelihood of contamination to the medications, solutions, fluids, etc., of the pre-filled or pre-dosed syringes is reduced compared to existing syringe designs. That is, an added protective barrier is present protecting the pre-dosed or pre-filled medication in the syringe while shelved. In order to maintain the plunger shaft in a withdrawn position and protect the pre-filled or pre-dosed medication, solution, or other substance, etc., from being inadvertently expelled or ejected from the syringe cavity due to impact or forces to the plunger shaft or other components of the syringe, a brace means can be incorporated which functions to restrict the plunger shaft from traversing the syringe cavity. As an example, a brace means such as a shrink film or tape, tube, cage, etc., can be applied over the corrugated sheath, plunger member, syringe barrel, or combination thereof, in a manner to restrict longitudinal movement of the plunger shaft or plunger member until the brace means is removed.

The syringes of the instant invention can be used for pre-packing or prepackaging medications which will be delivered or taken orally by the individuals. The syringes of the instant invention can be used as containers for holding medications such as antibiotics, etc., which will later be given orally to a patient. The pre-packing or prepackaging of the oral unit dose syringes can be performed or accomplished by a manufacturer which can provide pre-dosed or pre-filled unit dose oral medication syringes containing a desired medication, or the syringes can be used by pharmacy or other personnel or individuals to pre-dose and package oral medications. Because of the design of the syringes of the instant invention, the likelihood of contamination to the medications of the pre-filled or pre-dosed syringes is reduced when compared with existing syringe designs. That is, an added protective barrier is present protecting the pre-filled or prepackaged medication in the syringe while shelved.

The syringes of the instant invention may also be provided with syringe caps which fit or screw onto the reduced diameter neck portion of the forward end opening and function as closures. The syringe caps also function to preserve sterility of the outer surface of the reduced diameter neck and the inner cavity of the syringe barrel.

The syringes of the instant invention can be used advantageously by personnel working in labs, working with radioactive pharmaceuticals, performing tests in hospital labs, doing research in pharmaceutical companies, universities, and any other type of research facility performing research in any capacity such as biological, pharmaceutical, genetic, etc., that require the use of syringes.

Trained personnel, such as those working in hospitals, compounding establishments, etc., can also use the syringes of the instant invention to pre-fill or pre-dose the syringes of the instant invention with injectable or oral medications for delivery to a patient, nursing unit, doctor's office, other ordering establishment, etc. These personnel can also use the syringes of the instant invention to prepare intravenous admixtures, withdraw blood from patients, inject intravenous medications into patients, inject intramuscular medications into patients, prepare irrigation solutions, prepare dialysis fluids, prepare intravenous pushes, prepare bolus fluids, prepare intravenous fluids for parenteral injection, prepare immunizations for any route of administration, prepare oral dose medications, etc.

BRIEF DESCRIPTION OF THE DRAWINGS

Throughout the drawing figures, like reference numerals refer to like parts. The design features of the embodiments represented in the drawings are not intended to be restrictive to the inventive concept and other variations or modifications to the design features shown may be applied.

FIG. 1 is a cross-sectional view of a syringe of the instant invention having a corrugated sheath, cover, or shield concentrically enveloping a plunger shaft. The plunger is shown fully inserted into the syringe barrel cavity.

FIG. 2 is a cross-sectional view of the syringe of FIG. 1 with a greater length of the plunger member extending from the large rearward end opening of the syringe barrel while the corrugated sheath is shown in an elongated state maintaining the concentric envelopment of the plunger shaft. The plunger and piston are shown displaced from their original positions having been moved down the syringe cavity.

FIG. 3 is a cross-sectional view of a second embodiment of the instant invention showing a syringe having a straight barrel segment and a corrugated barrel segment. The plunger is shown fully inserted into the syringe barrel cavity.

FIG. 4 is a cross-sectional view of the syringe of FIG. 3 with the corrugated segment in an elongated state concentrically enveloping the plunger shaft. The plunger and piston are shown displaced from their original positions having been moved down the syringe cavity.

FIG. 5 is a cross-sectional view of a third embodiment of the instant invention showing a syringe having mating concentric plunger and syringe barrel walls.

FIG. 6A is a cross-sectional view of the syringe of FIG. 5 with the plunger member displaced from its original position having been moved along the glide space located between the external wall surface of the syringe barrel and the internal wall surface of the plunger member. The piston and plunger are shown displaced from their original positions having been moved down the syringe barrel cavity and away from the tapered internal walls of the syringe barrel cavity in cooperation with the plunger member displacement.

FIG. 7 is a cross-sectional view of a fourth embodiment of the instant invention showing a syringe having concentric syringe barrels and a mating plunger member. The plunger shaft and piston are shown fully inserted into the syringe barrel cavity.

FIG. 8A is a cross-sectional view of the syringe of FIG. 7 with the plunger member displaced from its original position having been moved along the glide space located between the external wall surface of the inner syringe barrel and the internal wall surface of the outer syringe barrel. The piston and plunger are shown displaced from their original positions having been moved down the inner syringe barrel cavity and away from the tapered internal walls of the inner syringe barrel cavity in cooperation with the plunger member displacement.

FIG. 10A is a view down the longitudinal axis of the syringe of FIG. 9 as viewed from the cross-section taken along 10-10 showing the semi-rigid, flexible material encircling the ribs of the plunger shaft.

DETAILED DESCRIPTION OF THE INVENTION

Figure 6B:
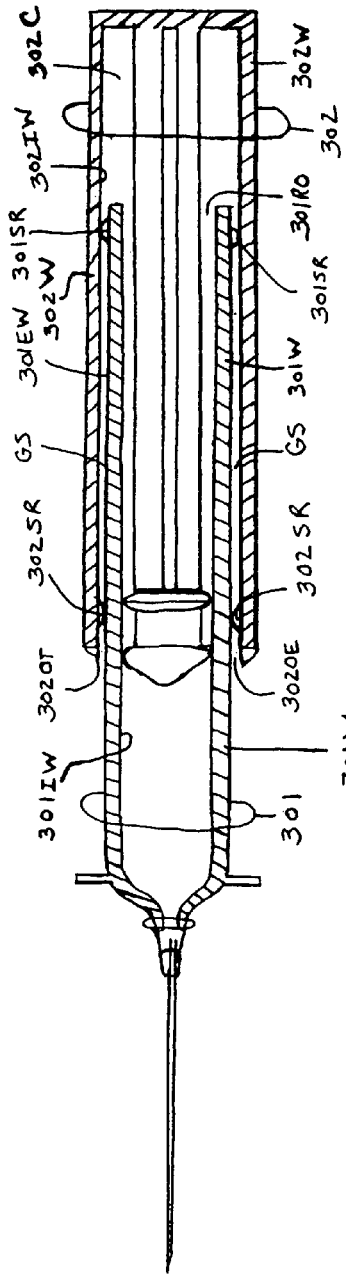
FIG. 6B is a view of FIG. 6A with sealing rings positioned on the syringe barrel and plunger member walls.

The following descriptions are presented to enable any person skilled in the art to make and use the invention, and are provided in the context of a particular application and its requirements. Various modifications to the disclosed embodiments will be readily apparent to those skilled in the art, and the general principles defined herein may be applied to other embodiments and applications without departing from the spirit and scope of the invention. The present invention is not intended to be limited to the embodiments described, but to be accorded the widest scope consistent with the principles and features disclosed herein.

For the purpose of describing how to use the syringes of each of the following embodiments, all of the embodiments will be described in accordance with the invention by making reference only to drawing liquid medication into the syringe and ejecting it out of the syringe. It is noted, however, that the syringes of the instant embodiments are compatible with performing other tasks requiring the use of a syringe, such as: withdrawing blood from patients, performing irrigations, injecting intravenous medications into patients, preparing irrigation solutions, preparing dialysis fluids, preparing intravenous pushes, preparing bolus fluids, preparing intravenous fluids for parenteral injection, drawing up oral medications for oral dispensing, prepacking or prefilling the syringe with medication or other fluids for oral or intravenous or intramuscular or subcutaneous uses, etc.

Syringe Having a Corrugated Sheath, Cover, or Shield

A new and improved syringe of the instant invention, as shown by FIG. 1, illustrates a syringe 100 formed of a cylindrical syringe barrel 101 and a cylindrical plunger shaft 103 having ribs. It is noted, however, that ribs are not required and the plunger shaft 103 can have any desired shape for its external surfaces such as cylindrical, square, triangular, etc. The syringe barrel 101 has external wall surfaces 101EW, internal wall surfaces 101IW, and a syringe cavity 102 in which a plunger shaft 103 and a plunger piston 104P, attached to the forward end terminus of the plunger shaft 103, are positioned. The head 104HP of the plunger piston 104P is in contact with the tapered forward end internal walls 101TIW of the syringe barrel 101. The tapered forward end walls 101TIW of the syringe barrel 101 taper to form a reduced diameter neck 101RDN with forward end opening 101FO at the forward end terminus of the syringe barrel 101. The tapered forward end external walls 101TEW of the reduced diameter neck 101RDN mate with the hub 105H of a needle 105 through frictional engagement. A circumferential wall can be formed around the external walls of the reduced diameter neck 101RDN. Threads or grooves are formed on the inside surfaces of the encircling circumferential wall such that the hub 105H of the needle 105 can be rotated or twisted on the threads or grooves and locked onto the tapered external wall surfaces 101TEW of the reduced diameter neck 101RDN and within the circumferential wall. Alternatively, threads or grooves can be formed on the tapered external wall surfaces 101TEW and on the inner wall surfaces of the hub 105H. The rearward end terminus 101RT of the walls 101W of the syringe barrel 101 is molded to the forward face surface 106FF of a syringe barrel handle member 106. The syringe barrel handle member 106 can be formed continuously with the syringe barrel walls 101W during the syringe barrel molding process or added in a separate molding step. Molded to the rearward face surface 106RF of the syringe barrel handle member 106, is a forward end terminus 107FT of a corrugated sheath 107. The rearward end terminus surface 107RT of the corrugated sheath 107 is molded to the forward face surface 108FF of a plunger handle member 108. The corrugated sheath, cover, or shield 107 concentrically envelops the rearward end portion of the plunger shaft 103RP when the plunger shaft 103 and piston 104P are fully inserted into the syringe barrel, as shown in FIG. 1. The forward end terminus 107FT of the corrugated sheath, cover, or shield 107 is attached by molding, fusing, adhesives, ultrasonic bonding or welding, thermal bonding, etc., to the rearward face surface 106RF of the syringe barrel handle member 106 which is formed or molded on the rearward end terminus 101RT of the walls 101W of the syringe barrel 101. The rearward end terminus 107RT of the corrugated sheath, cover, or shield 107 is attached by molding, fusing, adhesives, ultrasonic bonding or welding, thermal bonding, etc., to the forward face surface 108FF of the plunger handle member 108 which is molded, or formed, on the rearward end terminus 103RT of the plunger shaft 103. The rearward end terminus 103RT of the plunger shaft 103 is centrally molded and normal to the forward face surface 108FF of the plunger handle member 108. The forward end of the body of the plunger shaft 103 extends into the syringe cavity or hollow portion 102 of the syringe barrel 101. The corrugated sheath, cover, or shield 107 encloses and surrounds the rearward end portion 103RP of the plunger shaft 103 along the longitudinal axis of the portion of the plunger shaft 103 extending between the syringe barrel handle member 106 and the plunger handle member 108. The sheath 107 houses, encloses, or surrounds the portion of the plunger shaft 103 within the central cavity or hollow 107C of the corrugated sheath 107 when the corrugated sheath 107 is in a compressed state and in a lengthened state. The plunger shaft 103 is withdrawn from the syringe barrel cavity or hollow 102 by grasping the external walls of the syringe barrel 101EW with one hand and the plunger shaft handle member 108 and/or the outer surface of the corrugated sheath 107EW with the other hand and pulling the plunger shaft handle member 108 and/or corrugated sheath 107 such that the longitudinal length of the plunger shaft 103 traverses the cavity or hollow 102 of the syringe barrel 101 and progressively emerges from the rearward end opening 101RO of the syringe barrel 101. The peaks 107P and walls 107W of the pleats, corrugations, or folds in the sheath 107 are caused to separate along the longitudinal axis of the sheath 107 thereby lengthening the sheath 107 along its longitudinal axis. The plunger shaft 103 remains centrally located within the hollow or cavity 107C of the corrugated sheath 107 as the plunger shaft 103 emerges from the cavity 102 and rearward end opening 101RO of the syringe barrel 101. As the corrugations or folds separate, the corrugated sheath 107 lengthens enabling the plunger shaft 103 to be withdrawn from the hollow or cavity 102 of the syringe barrel 101, as depicted in FIG. 2. The corrugated sheath 107 lengthens and encloses a greater length of the plunger shaft 103 as the plunger shaft 103 is further withdrawn from the syringe barrel hollow 102. As the plunger shaft 103 is withdrawn from the syringe barrel hollow 102, a space 101S is formed between the piston head 104HP of the plunger piston 104P and the tapered internal walls 101TIW of the syringe barrel 101. The sheath 107 remains in the lengthened or elongated position until a force is used to compress or collapse the walls 107W of the folds or corrugations of the sheath 107 together. That is, it is not necessary for an individual to hold the withdrawn plunger 103 or lengthened corrugated sheath 107 such that it remains in its withdrawn and lengthened state, respectively. The corrugated sheath 107 is designed and manufactured such that it does not automatically recoil to its compressed or shortened state after being elongated. A force must be applied along the longitudinal axis of the syringe to cause the elongated corrugated walls 107W to be moved toward each other such that the corrugated sheath 107 compresses and shortens. When the walls 107W of the corrugated sheath 107 are forced together, the sheath 107 shortens. Shortening of the corrugated sheath 107 can be performed by applying pressure to the rearward end face surface 108RF of the plunger handle member 108 in the direction toward the rearward end opening 101RO of the syringe barrel 101 to cause the sheath to shorten and the plunger shaft 103 and the piston 104P to traverse the syringe barrel cavity 102 toward the tapered internal wall 101TIW surfaces of the syringe cavity 102 and the syringe entrance/exit port 101EP or forward end opening 101FO. The piston rim 104PR slidably engages and maintains a tight seal with the internal wall surfaces 101IW of the syringe barrel cavity 102 as the piston 104P advances. Liquid medication in the cavity 102 remains forward of the piston head 104HP during advancement of the plunger 103 and piston 104P such that the medication in the syringe barrel cavity 102 is ejected from the syringe cavity 102 through the entrance/exit port 101EP or forward end opening 101FO. An advantage of using the corrugated sheath 107 is the protection provided by the sheath 107 to the plunger shaft 103 and the internal cavity wall surfaces 101IW of the syringe barrel 101 in that contaminants deposited onto the external wall surface 107EW of the corrugated sheath 107 or the external wall surface 101EW of the syringe barrel 101 will not jeopardize the sterility of the inner cavity 102 of the syringe barrel 101 because the contaminants cannot penetrate the walls of the corrugated sheath 107 or the syringe barrel 101. It is also noted that the peaks, pleats, valleys, and walls of the corrugations can have any desired shape such as curved, triangular, square, etc, so long as the desired mechanical functioning of the corrugated sheath as set forth above is not compromised.

Syringe Having a Straight Segment and Corrugated Segment Syringe Barrel

A second embodiment of the instant invention, as shown by FIG. 3, illustrates a new and improved syringe 200 formed of a cylindrical syringe barrel 201 and a cylindrical plunger member 205. The syringe barrel 201 is formed with a straight segment 202 and a corrugated segment 203. The straight segment 202 is located on the forward end section of the syringe barrel 201 and the corrugated segment 203 is located at the rearward end section of the syringe barrel 201. The rearward end terminus 201RT of the syringe barrel 201 is molded to the forward face surface 204FF of a plunger handle member 204. The rearward end terminus 205RT of the plunger shaft 205 is centrally molded to the forward face surface 204FF of the plunger handle member 204. A rearward end portion 205RP of the plunger shaft body 205 is enclosed or surrounded by the corrugated segment 203 of the syringe barrel 201. The syringe barrel 201 has a forward open end 201FO and a rearward closed end 201RC. The rearward closed end 201RC is closed by the plunger shaft handle member 204 which is molded to the rearward end terminus 201RT of the syringe barrel 201. The open end 201FO is located at the forward end terminus 201FT of the syringe barrel 201. The forward end of the syringe barrel 201 tapers to a reduced diameter neck 201RDN at the entrance/exit port 201EP and forms a mating surface for the hub 208H of a needle 208. A forward end portion 205FP of the plunger shaft body 205, and a plunger piston 205P located at the forward end terminus 205FT of the plunger shaft 205, is enclosed or surrounded by the straight segment 202 of the syringe barrel 201. The plunger piston 205P and plunger shaft body 205 are caused to traverse the syringe barrel cavity or hollow 207 by grasping the syringe barrel external wall surface 201EW along the straight segment 202 with one hand and the plunger shaft handle member 204 and/or corrugated segment 203 with the other hand and pulling the plunger shaft handle member 204 and/or corrugated segment 203 such that the rearward end terminus 205RT of the plunger shaft 205 and the forward face surface 204FF of the handle member 204 moves away from the straight segment 202 of the syringe barrel 201 causing lengthening of the syringe barrel 201 and elongation of the corrugated segment 203, as shown in FIG. 4. Simultaneously, the plunger piston rim 205PR slidably engages the internal wall surfaces 201IW of the straight segment 202 of the syringe barrel 201 as it traverses the cavity or hollow 207 of the syringe barrel 201. In order to assist the user in lengthening of the syringe 200, a syringe barrel handle member (not shown) can be molded to the external surface of the syringe barrel wall surface 201EW along the straight segment 202. The syringe barrel handle member (not shown) can be used as a wall for leverage to assist the user in lengthening or shortening the syringe barrel 201 while pulling or pushing the plunger shaft handle member 204. The syringe barrel handle member can take any desired shape such as flat wall or plate, curved, or finger grip design, as examples. The peaks or pleats 203P, valleys 203V, and walls 203W of the corrugations, pleats, or folds in the corrugated segment 203 of the syringe barrel 201 are caused to separate along the longitudinal axis of the syringe barrel 201 as the plunger handle member 204 is pulled thereby lengthening the syringe barrel 201 along its longitudinal axis, as shown in FIG. 4. At least a portion of the plunger shaft 205 remains centrally located within, and the rim 205PR of the piston 205P remains in contact with, the internal wall surfaces 201IW of the hollow or cavity 207 of the syringe barrel straight segment 202 during elongation or lengthening of the syringe barrel 201. The rearward end terminus 205RT of the plunger shaft 205 and the syringe barrel rearward end terminus 201RT of the corrugated segment 203 remain molded to the forward end face surface 204FF of the plunger handle member 204. As the corrugations or folds of the corrugated segment 203 are caused to separate, the corrugated segment 203 of the syringe barrel 201 lengthens causing the forward portion of the plunger shaft 205FP to traverse the straight segment 202 of the syringe barrel cavity 207, and the plunger piston 205P attached to the forward end terminus 205FT of the plunger shaft 205 to slide along the straight segment 202 of the syringe barrel cavity 207 in the direction of the corrugated segment 203. This is because the rearward end terminus 205RT of the plunger shaft 205 is centrally molded to the forward face surface 204FF of the plunger handle member 204 which moves in a direction away from the straight segment 202 of the syringe barrel 201 during lengthening causing the plunger 205 and piston 205P to traverse the syringe barrel cavity 207 toward the corrugated segment 203. The plunger piston 205P is in contact and forms a seal with the internal cavity walls 201IW of the syringe barrel 201. The corrugated segment 203 encloses or encircles a greater length of the plunger shaft body 205 as the plunger is drawn further along the syringe barrel hollow or cavity 207, as shown in FIG. 4. The corrugated segment 203 remains in the lengthened or elongated state until a force is used to compress or collapse together the folds or corrugations of the corrugated segment 203, which shortens the syringe barrel 201. That is, it is not necessary for the individual pulling the plunger handle member 204 and lengthening the corrugated segment 203 to hold the plunger handle member 204 or corrugated segment 203 such that the corrugated segment 203 remains in its lengthened position or elongated state. The corrugated segment 203 is designed and manufactured such that it does not automatically recoil from an elongated position. An axial force must be applied to the syringe barrel 201 to cause the corrugated walls of the elongated corrugated segment 203 to move toward each other or together such that the syringe barrel 201 shortens along its longitudinal axis. As the walls of the corrugated segment 203 are forced together, the syringe barrel 201 shortens. Shortening of the corrugated segment 203 is performed by pressing the rearward end face surface 204RF of the plunger shaft handle member 204 along the longitudinal axis of the syringe barrel 201 to cause the corrugated segment 203 to shorten and the plunger piston 205P to slide along the internal cavity walls 201IW of the syringe barrel cavity 207 toward the forward end terminus 201FT and toward the syringe barrel entrance/exit port 201EP such that medication in the syringe barrel cavity 207 is ejected from the syringe 200 through the entrance/exit port 201EP or forward end opening 201FO.

In operation, medication is drawn up from a vial or ampoule, for example, by first introducing the needle 208, which is attached to the reduced diameter neck 201RDN of the entrance/exit port 201EP, into the vial or ampoule containing the medication. Next, the corrugations or folds of the corrugated segment 203 of the syringe barrel 201 are caused to separate by pulling the plunger handle member 204. This also causes the plunger shaft 205 and piston 205P to traverse the syringe barrel cavity 207 along the straight segment 202 and away from the tapered internal walls 201TIW of the syringe barrel cavity 207 and toward the corrugated segment 203. As the plunger piston 205P traverses the syringe barrel cavity 207, the plunger piston rim 205PR slidably engages and maintains a tight seal with the internal wall surfaces 201IW of the syringe barrel cavity 207. This causes the air column in the bore or cavity 207 located behind the plunger piston 205P and adjacent the body of the plunger shaft 205 to be pushed into the elongated corrugated segment 203 of the syringe barrel 201. A vacuum is created in the space located between the forward end of the piston head 205HP and the tapered internal wall surface 201TIW of the syringe barrel 201 as the piston head 205HP is pulled away from the tapered internal walls 201TIW. The vacuum created causes the liquid medication in the vial to be drawn into the syringe barrel cavity 207 through the needle 208, which is frictionally attached to the outer walls of the reduced diameter neck 201RDN, and the entrance/exit port 201EP. The needle 208 is then removed from the medication vial and positioned in the needle port of an appropriate bag or bottle of intravenous solution. The liquid medication is then injected into the bag or bottle of intravenous solution. The reduced diameter neck 201RDN is manufactured or molded to operate with any existing line of hypodermic needles, tubing, or caps or closures.

An advantage of using the syringe 200 having a corrugated segment 203 and a straight segment 202 is the protection provided to the plunger shaft 205 and the internal cavity wall surfaces 201IW in that contaminants deposited onto the external wall surfaces of the syringe barrel 201EW will not jeopardize the sterility of the inner cavity 207 of the syringe barrel 201 because the contaminants cannot penetrate the walls 201W of the syringe barrel 201. It is also noted that the peaks, pleats, valleys, and walls of the corrugations of the corrugated segment 203 can have any desired shape such as curved, triangular, square, etc, so long as the desired mechanical functioning of the corrugated segment as set forth above is not compromised.

Syringe Having Syringe Barrel and Plunger Member

A third embodiment of the instant invention, as shown by FIGS. 5, 6A and 6B, illustrates a new and improved syringe 300 formed of a cylindrical syringe barrel 301 and a cylindrical plunger member 302. The syringe barrel 301 and the plunger member 302 have mating concentric plunger member and syringe barrel walls 302W and 301W, respectively. The plunger member 302 has a wall 302W having an open-end 302OE and a closed end 302CE. The closed end 302CE of the plunger member 302 has a flat bottom floor structure 304 forming a cup-shaped inner cavity. The flat bottom floor structure 304 has forward and rearward face surfaces 304FF and 304RF, respectively. The flat bottom floor structure 304 can be molded continuous with the plunger member cylindrical walls 302W. The inside diameter of the plunger member 302 is constant along its length. The forward face surface 304FF of the flat bottom floor structure 304 has molded thereto the rearward end terminus 305RT of a plunger shaft 305. The plunger shaft 305 is concentrically surrounded by the internal face wall surfaces 302IW of the plunger member 302 along its longitudinal length. The plunger shaft 305 extends centrally from the forward face surface 304FF of the flat bottom floor structure 304 along the length of the internal face wall surfaces 302IW of the plunger member 302 which concentrically surround, enclose, or house the plunger shaft 305. The plunger shaft 305 has a piston 305P attached to its forward end terminus 305FT by mounting, fusing, molding, adhesives, ultrasonic bonding or welding, thermal bonding, etc. The position of the piston rim 305PR of the piston head 305HP coincides with the open end terminus 302OT of the plunger member wall 302W. The syringe barrel 301 is formed with two open ends at opposite ends of the syringe bore or cavity 301C— one having a smaller forward end diameter opening 301FO. The rearward end larger diameter opening 301RO is located at the rearward end terminus 301RT of the syringe barrel 301. The smaller forward end diameter opening 301FO has a reduced diameter neck 301RDN at the entrance/exit port 301EP. The forward end smaller diameter opening 301FO is located at the forward end terminus 301FT of the syringe barrel 301. The syringe barrel 301 has an outside wall diameter less than the inside wall diameter of the plunger member 302 along the entire length of the syringe barrel 301. The inside diameter of the syringe barrel 301 is slightly less than the diameter of the piston rim portion 305PR of the plunger piston 305P attached by mounting, fusing, molding, adhesives, ultrasonic bonding or welding, thermal bonding, etc., at the forward end terminus 305FT of the plunger shaft 305. The piston rim portion 305PR of the plunger piston 305P mates with and forms a seal with the internal wall surfaces 301IW of the bore or cavity 301C of the syringe barrel 301. The internal and external wall surfaces 301IW and 301EW of the syringe barrel 301 taper at the syringe barrel forward end forming the reduced diameter neck 301RDN having the smaller diameter forward end opening 301FO and an entrance/exit port 301EP through which fluid medications and other solutions or fluids enter and exit the cavity 301C of the syringe barrel 301. The external wall surface 301EW of the reduced diameter neck 301RDN forms a mating surface for the hub 307H of a needle 307. At a point rearward to the forward end small diameter opening 301FO of the syringe barrel 301, a handle member 301H is provided for assisting the user in sliding of the plunger member 302 relative to the syringe barrel 301.

The plunger member 302 is mated with the syringe barrel 301 by fitting the plunger piston 305P located at the forward end terminus of the plunger shaft 305FT into the central cavity or bore 301C of the syringe barrel 301. As the piston 305P and plunger shaft 305 are slid into the central cavity 301C of the syringe barrel 301, the internal wall surfaces 302IW of the plunger member 302 form a face-to-face relationship with the external wall surfaces 301EW of the syringe barrel 301. The full length of the plunger shaft 305 and piston 305P slide into the full length of the central cavity 301C of the syringe barrel 301 such that the head of the piston 305HP abuts the tapered internal walls 301TIW of the syringe barrel 301. The contour of the piston head 305HP of the piston 305P matches and follows the contours of the tapered internal wall 301TIW of the syringe barrel 301 to form a seal at the forward end opening 301FO which is the entrance/exit port 301EP. The terminus surfaces 301RT of the rearward larger diameter opening 301RO can abut with the forward face surface 304FF of the flat bottom floor structure 304 of the plunger member 302. In operation the plunger member wall 302W concentrically surrounds the syringe barrel wall 301W. Medication or other fluid is drawn up from a vial or ampoule, for example, by first introducing the needle 307, which is attached to the external walls of the reduced diameter neck 301RDN, into the vial containing the medication. Next, the internal wall surface of the plunger member 302IW is concentrically slid alongside the length of the external wall surface of the syringe barrel 301EW while maintaining a concentric glide space GS between the internal wall surface 302IW of the plunger member 302 and the external wall surface 301EW of the syringe barrel 301. Simultaneously, the piston rim 305PR of the plunger piston 305P, which is attached at the forward end terminus of the plunger shaft 305FT, slidably engages and maintains a tight seal with the internal wall surfaces 301IW of the syringe barrel cavity 301C while moving along the syringe barrel cavity 301C and away from the tapered internal walls 301TIW of the syringe barrel 301, as shown in FIG. 6A. This causes the air column in the bore or cavity 301C located behind the plunger piston 305P and adjacent the plunger shaft 305 to be expelled or pushed out of the cavity 301C. A vacuum is created in the space located between the forward end of the piston head 305HP and the tapered internal wall surfaces 301TIW of the syringe barrel 301. The vacuum causes the liquid medication or other fluid in the vial or ampoule to be drawn into the syringe barrel cavity 301C through the needle 307, hub 307H, and entrance/exit port 301EP. The needle 307 is then removed from the medication vial or ampoule and positioned in the needle port of an appropriate bag or bottle of intravenous solution. By applying pressure to the rearward face surface of the flat bottom floor structure 304RF, the liquid medication can then be injected into the bag or bottle of intravenous solution. This pressure causes the longitudinal length of the plunger shaft 305 and the plunger piston 305P to advance along the syringe barrel cavity 301C toward the tapered internal wall surfaces 301TIW of the syringe cavity 301C. The piston rim 305PR slidably engages and maintains a tight seal with the internal wall surfaces 301IW of the syringe cavity 301C as the piston 305P advances. The liquid medication remains forward of the piston head 305HP during advancement of the plunger 305 and piston 305P.

An advantage of using the syringe 300 having mating concentric plunger and syringe barrel walls 302W and 301W, respectively, is the protection provided to the plunger shaft 305 and the internal cavity wall surfaces 301IW of the syringe barrel 301 in that contaminants deposited onto the external wall surfaces 302EW of the plunger member 302 or external wall surfaces of the syringe barrel 301EW will not jeopardize the sterility of the syringe barrel cavity 301C because the design discourages entry of contaminants into the syringe barrel cavity 301C.

An added feature for the third embodiment, as shown by FIG. 6B, is to provide a first sealing ring 302SR projecting perpendicularly from the inner wall surface 302IW of the plunger member 302 at or near the open end terminus 302OT of its open end 302OE. The sealing ring 302SR is a continuous ring that follows the complete circumference of the internal wall 302IW of the plunger member 302. A second sealing ring 301SR is formed projecting perpendicularly from on the external wall surface 301EW of the syringe barrel 301 at or near its rearward end large diameter opening 301RO. The sealing rings 301SR and 302SR provide several advantages. When the walls 302W of the plunger member 302 are concentrically mated with the walls 301W of the syringe barrel 301, the sealing rings 302SR and 301SR project or extend into the glide space GS. First, the sealing rings 301SR and 302SR seal the glide space GS existing between the internal wall surface 302IW of the plunger member 302 and the external wall surface 301EW of the syringe barrel 301. This discourages entry of contaminants such as dirt, dust, microorganism, and pathogens carried by the air, hands, fingers, gloves, etc., from becoming deposited onto the internal surfaces 301IW of the syringe barrel cavity 301C. Second, the sealing rings 302SR and 301SR function to prevent accidental separation of the plunger member 302 from the syringe barrel 301 through abutment of the sealing rings 301SR and 302SR as the walls of the plunger member 302W are moved relative to the walls of the syringe barrel 301W. Third, the sealing rings 301SR and 302SR function as a dam or barrier to fluids that collect or accumulate in the cup of the inner cavity 302C of the plunger member 302 due to piston failure.

The sealing rings 301SR and 302SR can be formed of a rigid, semi-rigid, or flexible material. The sealing ring flexible material has bendable characteristics and can provide a sweeping, wiping action to the surface for which it contacts.

Syringe Having Concentric Syringe Barrels and a Plunger Member

Figure 8B:
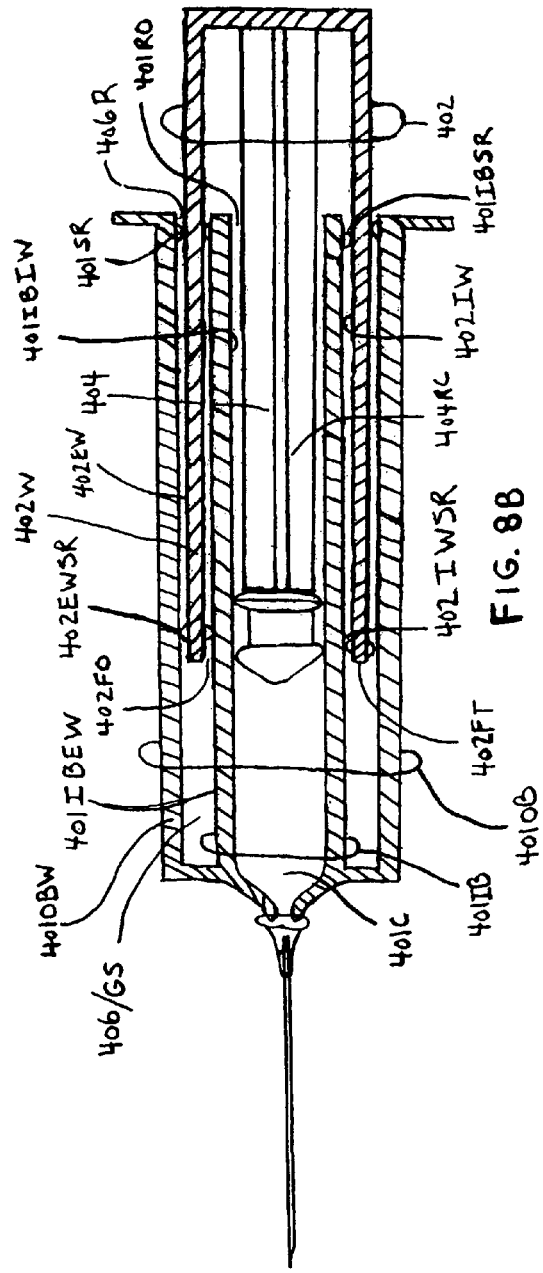
FIG. 8B is a view of FIG. 8A with sealing rings positioned on the concentric syringe barrel walls and the plunger member walls.

A fourth embodiment of the instant invention, as shown by FIGS. 7, 8A and 8B, illustrates a new and improved syringe 400 formed of cylindrical concentric syringe barrels 401OB and 401IB and a cylindrical plunger member 402. The plunger member 402 has a wall 402W with a forward open-end 402FO and a rearward closed end 402RC. The rearward closed end 402RC of the plunger member 402 has a flat bottom floor structure 403 forming a cup. It is noted that other shapes can be used for the bottom floor structure; and thus, the shapes are not restricted to flat. The flat bottom floor structure 403 has forward end and rearward end face surfaces 403FF and 403RF, respectively. The flat bottom floor structure 403 can be molded continuous with the walls of the plunger member 402W. The inside diameter of the plunger member walls 402W is constant along the length of the plunger member 402. The forward end face surface 403FF of the flat bottom floor structure 403 has molded thereto the rearward end terminus 404RT of a plunger shaft 404. The plunger shaft can also be molded continuous the flat bottom floor structure 403. The plunger shaft 404 is centrally located within and surrounded by the internal face surfaces of the walls 402IW of the plunger member 402 which extend normal from the forward end face 403FF of the flat bottom floor structure 403. The plunger shaft 404 extends centrally and normal from the forward end face surface 403FF of the flat bottom floor structure 403 along the length of the internal wall face surfaces 402IW of the plunger member 402. The walls 402W of the plunger member 402 concentrically surround the plunger shaft 404. The plunger shaft 404 has a piston 404P attached to its forward end terminus 404FT by mounting, fusing, molding, adhesives, ultrasonic bonding or welding, thermal bonding, etc. The position of the piston rim 404PR of the plunger piston 404P coincides with the forward end terminus 402FT of the wall of the plunger member 402W at its forward open end 402FO. An inner concentric syringe barrel 401IB is formed with two open ends located at opposite ends of the inner concentric syringe barrel cavity 401C—the rearward end opening 401RO having a larger diameter opening than the forward end opening 401FO. The rearward end larger diameter opening 401RO is located at the rearward end terminus 401RT of the inner concentric syringe barrel 401IB. The forward end smaller diameter opening 401FO is located at the forward end terminus 401FT of the concentric syringe barrel 401OB and 401IB which has a reduced diameter neck 401RDN at the entrance/exit port 401EP. The concentric syringe barrel is formed with inner and outer syringe barrels 401IB and 401OB, respectively. The inner syringe barrel 401IB has an outside diameter less than the inside diameter of the plunger member walls 402W along the entire length of the inner syringe barrel 401IB. The inside diameter of the inner syringe barrel 401IB is slightly less than the diameter of the rim portion 404PR of the plunger piston 404P attached by mounting, fusing, molding, adhesives, ultrasonic bonding or welding, thermal bonding, etc., at the forward end terminus 404FT of the plunger shaft 404. The piston rim portion 404PR of the plunger piston 404P mates with and forms a seal with the inner barrel internal wall surfaces 401IBIW of the bore or cavity 401C of the inner syringe barrel 401IB. The internal and external wall surfaces of the inner syringe barrel 401IBIW and 401IBEW, respectively, taper at their forward ends forming the reduced diameter neck 401RDN having the forward end smaller diameter opening 401FO and an entrance/exit port 401EP through which fluid medications and other solutions or fluids enter and exit the cavity 401C. The external wall surface of the reduced diameter neck 401RDN forms a mating surface for the hub 405H of a needle 405. The outer syringe barrel 401OB concentrically encircles the inner syringe barrel 401IB forming concentric syringe barrels. The internal wall surfaces 401OBIW of the outer syringe barrel 401OB are in face-to-face relationship with the external wall surfaces 401IBEW of the inner syringe barrel 401IB and are separated by a distance which forms a second cavity or glide space 406/GS between the wall of the inner syringe barrel 401IB and the wall of the outer syringe barrel 401OB. This second cavity or space 406/GS is open at its rearward end 406R and closed at its forward end 406F forming a cup shape. The rearward open end 406R receives the walls 402W of the plunger member 402. This second cavity or space 406/GS functions as a glide space for the walls 402W of the plunger member 402. At a point located on the external wall surface 401OBEW of the outer syringe barrel 401OB, a handle member 401H is provided for assisting the user in sliding the plunger member 402 relative to the inner and outer syringe barrels 401IB and 401OB, respectively.

The plunger member 402 is mated with the concentric syringe member 401IB, 401OB by fitting the plunger piston 404P, located at the forward end terminus of the plunger shaft 404FT, into the central cavity or bore 401C formed by the walls 401IBW of the inner syringe barrel 401IB. As the piston 404P and plunger shaft 404 are slid into the central cavity 401C of the inner syringe barrel 401IB, the internal wall surfaces 402IW of the plunger member 402 form a face-to-face relationship with the external wall surfaces 401IBEW of the inner syringe barrel 401IB. Also, the external wall surfaces 402EW of the plunger member 402 form a face-to-face relationship with the internal wall surfaces 401OBIW of the outer syringe barrel 401OB. The full length of the plunger shaft 404 and piston 404P slide into the full length of the central cavity 401C of the inner syringe barrel 401IB such that the head of the piston 404HP abuts the tapered internal walls 401TIW of the inner syringe barrel 401IB. The contour of the head of the piston 404HP matches and follows the contours of the tapered internal walls 401TIW of the inner syringe barrel 401IB to form a seal at the forward end opening 401FO of the entrance/exit port 401EP. The rearward terminus surfaces 401RT of the rearward end larger diameter opening 401RO of the inner syringe barrel 401IB can abut with the forward face surface 403FF of the flat bottom floor structure 403 of the plunger member 402 with full insertion of the plunger shaft 404 into the central cavity or bore 401C of the inner syringe barrel 401IB. In operation, the walls of the inner and outer concentric syringe barrels 401IBW and 401OBW concentrically sandwich the plunger member walls 402W. In operation, medication is drawn up from a vial or ampoule, for example, by first introducing the needle 405, attached by the hub 405H to the reduced diameter neck 401RDN of the entrance/exit port 401EP, into the vial or ampoule. Next, the wall surfaces 402W of the plunger member 402 are concentrically slid within the glide space 406/GS existing between and along the length of the external wall surface 401IBEW of the inner syringe barrel 401IB and the internal wall surface 401OBIW of the outer syringe barrel 401OB, respectively, such that the concentric walls 402W of the plunger member 402 slide out of the glide space 406/GS. Simultaneously, the piston rim 404PR of the piston 404P, attached at the forward end terminus 404FT of the plunger shaft 404, slidably engages and maintains a tight seal with the internal wall surfaces 401IBIW of the inner syringe barrel 401IB while moving along the inner syringe barrel cavity 401C and away from the tapered internal wall 401TIW of the inner syringe barrel 401IB. This causes the air column in the bore or cavity 401C located behind the piston 404P and adjacent the plunger shaft 404 to be pushed out of the syringe cavity 401C creating a vacuum in the space located between the forward end of the piston head 404HP and the tapered internal wall surfaces 401TIW of the inner syringe barrel cavity 401C. The vacuum causes the liquid medication in the vial or ampoule to be drawn into the inner syringe barrel cavity 401C through the needle 405, hub 405H, and entrance/exit port 401EP. The needle 405 is then removed from the medication vial or ampoule and positioned in a needle port of an appropriate bag or bottle of intravenous solution. The liquid medication can then be injected into the bag or bottle of intravenous solution by applying pressure to the rearward face surface 403RF of the flat bottom floor structure 403. This pressure causes the longitudinal length of the plunger shaft 404 and the plunger piston 404P to advance within and along the inner syringe barrel cavity 401C toward the tapered internal wall surfaces 401TIW of the syringe cavity 401C. The piston rim 404PR slidably engages and maintains a tight seal with the internal wall surfaces of the inner barrel 401IBIW of the syringe cavity 401C as the piston 404P and plunger shaft 404 advance. The liquid medication remains forward of the piston head 404HP in the space located between the forward end of the piston head 404HP and the tapered internal walls 401TIW of the syringe barrel cavity 401C during advancement of the plunger shaft 404 and piston 404P. The liquid medication is ejected out of the entrance/exit port 401EP of the inner syringe barrel 401IB as the plunger shaft 404 is advanced.

An advantage of using a syringe having concentric inner and outer syringe barrels 401IB and 401OB, which functions concentrically with a plunger member 402, is the protection provided to the plunger shaft 404 and the internal wall surfaces 401IBIW of the syringe cavity 401C in that contaminants deposited onto the external wall surfaces 402EW of the plunger member 402 or the external wall surfaces 401OBEW of the outer syringe barrel 401OB will not jeopardize the sterility of the cavity 401C of the inner syringe barrel 401IB because the syringe design discourages entry of contaminants into the inner syringe barrel cavity 401C, ultimately protecting the medication.

An added feature for the fourth embodiment is to provide a first sealing ring 401SR projecting perpendicularly from the internal wall surface 401OBIW of the outer syringe barrel 401OB at or near the glide space 406/GS rearward end opening 406R. A second sealing ring 402EWSR can be formed projecting perpendicularly from the external wall surface 402EW of the plunger member 402 at or near the terminus of its forward open-end 402FO. A third sealing ring 402IWSR can be formed projecting perpendicularly from the internal wall surface 402IW of the plunger member 402 at or near the terminus of its open forward end 402FO. A fourth sealing ring 401IBSR can be formed projecting perpendicularly from the external wall 401IBEW surfaces of the inner syringe barrel 401IB at or near the rearward end terminus 401RT of its open-end 401RO. One or more of the above sealing rings can be formed or provided on the inner or outer barrel wall surfaces 401IB and 401OB of the syringe 400 or the plunger member walls 402W. The sealing rings provide several advantages. First the sealing rings seal the glide space 406/GS existing between the internal wall surface 401OBIW of the outer syringe barrel 401OB and the external wall surface 401IBEW of the inner syringe barrel 401IB. This discourages entry of contaminants such as dirt, dust, microorganisms, pathogens, and any other type of contaminant, carried by air, hands, fingers, gloves, etc., from becoming deposited onto the internal wall surfaces 401IBIW of the syringe barrel cavity 401C. Second, the sealing rings function to prevent accidental separation of the plunger member 402 from the concentric syringe barrels 401IB and 401OB through abutment of the sealing rings of the concentric syringe barrels 401IB and 401OB with the sealing rings of the plunger member 402 as the walls of the plunger member 402W are moved relative to the walls 401IBW and 401OBW of the inner and outer concentric syringe barrels 401IB and 401OB. Third, the sealing rings function as a dam or barrier to medications, fluids, or solutions that collect or accumulate in the cup of the plunger member 402 due to piston failure.

Syringe Having Contaminant Shield or Barrier

Figure 9:
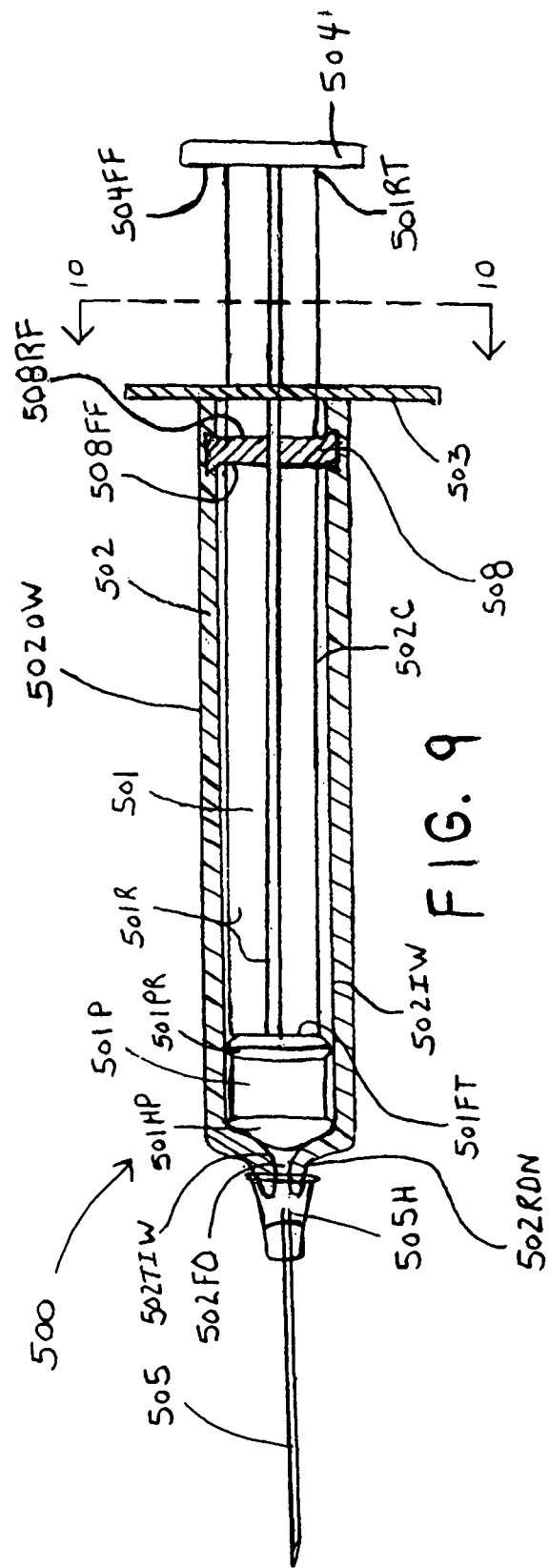
FIG. 9 is a longitudinal cross-sectional view of a fifth embodiment showing the contaminant shield molded in the syringe barrel cavity.
Figure 10B:
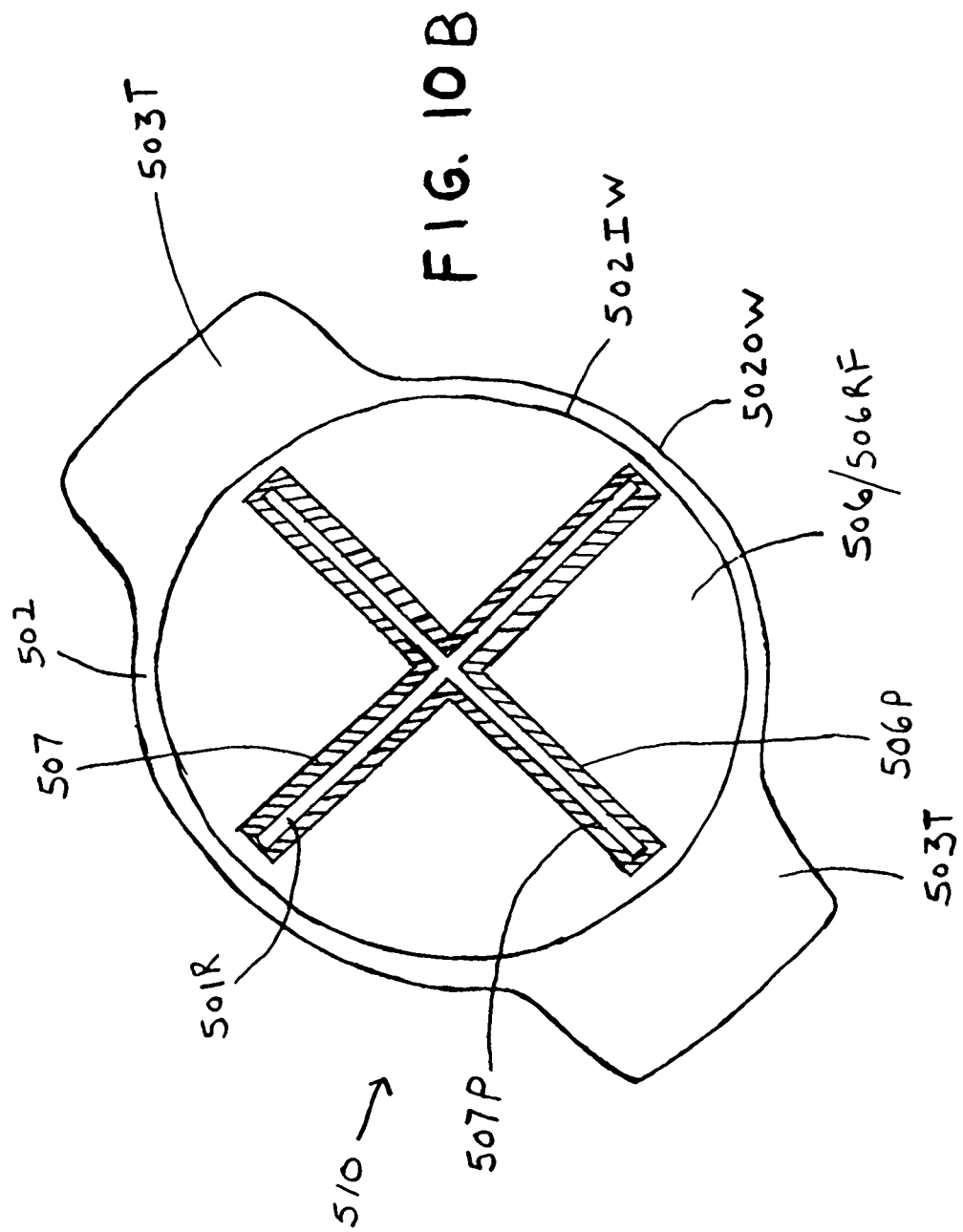
FIG. 10B is a view down the longitudinal axis of the syringe of FIG. 9 as viewed from the cross-section taken along 10-10 showing the rigid or hard first part with the second part attached to its periphery or edge.
Figure 11:
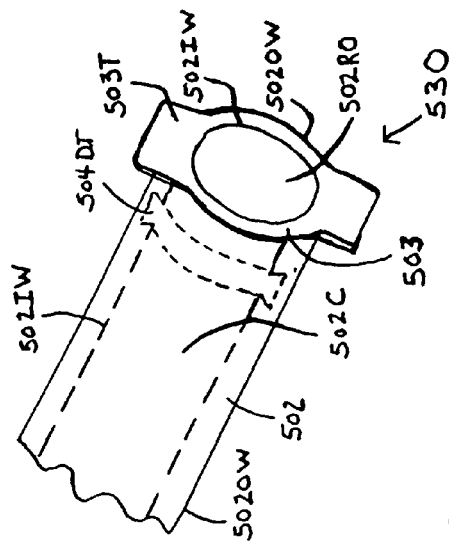
FIG. 11 is a view of a syringe barrel of the fifth embodiment depicting a dovetail groove formed in the inner wall of the syringe barrel cavity.

In a fifth embodiment of the instant invention, it is an object to provide a new and improved syringe having a contaminant shield positioned at or near the rearward end opening of the syringe barrel. FIG. 9 shows a longitudinal cross-section of the syringe of the fifth embodiment of the instant invention. FIGS. 10A and 10B are views along the longitudinal axis of the syringe of FIG. 9 as viewed from a cross-section taken along the line 10-10. The contaminant shield 520 is formed on the rearward end section of the syringe barrel inner wall surfaces 502IW of syringe barrel 502 with a semi-rigid and flexible material and projects perpendicularly from the circumference or perimeter of the syringe barrel inner wall surfaces 502IW into the syringe barrel cavity 502C and surrounds and abuts the surfaces and walls of the ribs 501R which form the spine of the plunger shaft 501. The contaminant shield 520 can be formed from a single material or a mixture of materials which will provide a semi-rigid and flexible characteristic to the shield walls 508. The shield walls have centrally formed therethrough an opening having the shape of the cross-section of the plunger shaft 501 used in conjunction with syringe 500. To facilitate attachment or molding of the contaminant shield walls 508 to the inner wall surface 502IW of the syringe barrel cavity 502C, a dovetail groove 504DT, or similar locking groove, can be formed on the surface of the inner wall 502IW, as shown in FIGS. 9 and 11, along the circumference or perimeter of the syringe cavity 502C at or near the rearward end opening 502RO of the syringe barrel 502. During the molding process, the dovetail groove 504DT formed in the inner wall surface 502IW of the syringe cavity 502C receives and anchors the material used to form the contaminant shield walls 508. The contaminant shield walls 508 have a forward end face surface 508FF facing into the syringe cavity 502C of the syringe barrel 502 and a rearward end face surface 508RF facing the plunger handle member 504. It is noted that the plunger shaft 501 can have any cross-sectional shape desired; such as cylindrical, ribs, triangular, square, etc. Accordingly, the periphery 508P of the opening formed in the contaminant shield walls 508 of contaminant shield 520 defines the cross-sectional shape of the plunger shaft 501.

Alternatively, the cover can be formed of two parts, as shown in FIG. 10B. The first part 506 is formed of a material providing a rigid or hard characteristic or quality to the contaminant shield 510. The first part 506 can be formed of the same material as, and molded continuous with the circumference inner wall surface 502IW of, the syringe barrel 502 at or near the rearward end opening 502RO of the syringe barrel 502. The first part 506, when formed, projects into the syringe barrel cavity 502C perpendicularly from the circumference or perimeter of the inner wall surface 502IW of the syringe barrel 502. The first part has a forward face surface (not shown) and a rearward face surface 506RF. The first part has centrally formed therethrough an opening having the shape of the cross-section of the plunger shaft 501 used in conjunction with the syringe 500. It is noted that the plunger shaft 501 can have any cross-sectional shape; such as ribbed, cylindrical, triangular, square, etc. Accordingly, the cross-section of the opening in the contaminant shield 510 corresponds to the plunger shaft cross-sectional shape. If the contaminant shield 510 is formed separately, or with a different material than that used to form the syringe barrel cavity 502C, then a dovetail groove 504DT, or any other similar locking groove, can be formed in the inner wall surface 502IW of the syringe barrel 502 along the circumference or perimeter of the barrel syringe inner wall surface 502IW at or near the rearward end opening 502RO of the syringe barrel 502. During the molding process, the dovetail groove 504DT receives and anchors the material used to form the first part 506 of the contaminant shield 510.

The second part 507 of the contaminant shield 510 is formed from a soft, flexible material that has a bendable characteristic. The second part 507 is formed within the cross-sectional opening and on the periphery of the first part 506. The second part 507 projects from the periphery 506P or edges of the first part and into the cross-sectional opening. The second part terminates as a flexible lip, edge, or periphery 507P that defines the cross-sectional opening. During operation or use, the lip, edge, or periphery 507P of the second part 507 is in contact with the surfaces of the ribs 501R of the plunger shaft 501 which fits within the cross-sectional opening and traverses the opening as the plunger shaft 501 exits and enters the syringe barrel cavity 502C. The second part 507 is formed on the cross-sectional periphery of the first part 506P as by providing a dovetailed shape, or other surface shape which provides a locking function, to the cross-sectional periphery 506P of the first part 506 during its forming operation to which the second part 507 can be subsequently formed about. This can be accomplished by providing the external surface of the first part at its edge or periphery with a dovetailed shape, or other surface shape such as slits or holes which would provide a locking mechanism or function to the cross-sectional periphery of the first part during its forming operation to which the second part can be formed about. Alternatively, a dovetailed groove, or similar locking groove, can be provided at and within the cross-sectional periphery 506P or edge of the first part 506 to receive and anchor the material used to form the second part 507 of the contaminant shield 510. The rearward end terminus 501RT of the plunger shaft 501 is centrally molded to the forward face surface 504FF of a plunger handle member 504 with the body of the plunger shaft 501 extending through the cross-sectional opening formed in the contaminant shield 510. The forward end terminus 501FT of the plunger shaft 501 has a piston 501P attached or formed thereto by mounting, fusing, molding, adhesives, ultrasonic bonding or welding, thermal bonding, etc., and, along with the plunger shaft, is movably fitted into the cavity, fluid reservoir, or hollow portion 502C of the syringe barrel 502. The syringe barrel 502 is formed with two open ends 502RO and 502FO located at opposite ends of the syringe cavity 502C. The rearward end of the syringe barrel 502 has a plunger shaft cross-sectional opening as described above and the forward end terminus of the syringe barrel 502 has a small diameter opening 502FO. The small diameter opening 502FO has a reduced diameter neck 502RDN having tapered internal walls forming the entrance/exit port for the syringe cavity 502C. The needle hub 505H of a needle 505 is attached to the reduced diameter neck 502RDN of the syringe 500. In operation, the plunger shaft 501 is withdrawn from the syringe barrel cavity 502C by grasping the outer syringe barrel surface 502OW with one hand and the plunger shaft handle member 504 with the other hand and pulling the plunger shaft handle member 504 such that the plunger shaft 501 emerges from the hollow or cavity 502C of the syringe barrel 502 through the rearward end plunger shaft cross-sectional opening formed in the contaminant shield 510 or 520 exposing the plunger shaft 501 to the external environment. During withdrawal, the piston 501P at the forward end terminus 501FT of the plunger shaft 501 slidably engages and maintains a tight seal with the internal wall surfaces 502IW of the syringe barrel cavity 502C while moving along the syringe barrel cavity 502C and away from the tapered internal walls 502TIW of the syringe barrel 502. This causes the air column in the syringe bore or cavity 502C behind the piston 501P and adjacent the plunger shaft 501 to be expelled or pushed out of the syringe cavity 502C through the plunger shaft cross-sectional opening creating a vacuum in the space located between the forward end of the piston head 501HP and the internal tapered wall surfaces 502TIW of the syringe barrel 502. The plunger shaft 501 remains in a withdrawn position until a force is applied along the longitudinal axis of the plunger shaft 501 in a direction toward the forward end terminus 501FT of the plunger shaft 501 to cause the plunger shaft 501 to pass through the plunger shaft cross-sectional opening formed in the contaminant shield 510 or 520 and cause the plunger shaft 501 and piston 501P to advance along the longitudinal axis of the syringe barrel cavity 502C toward the tapered internal wall surfaces 502TIW and entrance/exit port of the reduced diameter neck 502RDN of the syringe barrel 502. The inside diameter of the syringe barrel 502 is slightly less than the diameter of the rim portion 501PR of the piston 501P such that the piston rim 501PR slidably engages and maintains a tight seal with the internal wall surfaces 502IW of the syringe barrel cavity 502C as the piston 501P advances to maintain liquid medication or other fluid in the cavity 502C forward of the piston head 501HP during advancement of the plunger 501 and piston 501P such that the medication or other liquid in the syringe barrel cavity 502C is ejected from the syringe cavity 502C through the entrance/exit port located at the forward end opening 502FO. As the plunger shaft 501 and piston 501P advance along the internal wall surfaces 502IW of the syringe barrel cavity 502C, the semi-rigid flexible material 508 or the flexible second part 507, depending on which contaminant shield 510 or 520 design is used, contacts the rib surfaces 501R of the plunger shaft 501 while it is advanced through the plunger shaft cross-section of the contaminant shield 510 or 520 providing a wiping and sweeping action to the rib surfaces 501R of the plunger shaft 501 in a direction away from the forward end terminus 501FT of the plunger shaft 501 as the plunger shaft 501 and piston 501P are caused to traverse the syringe cavity 502C toward the forward end terminus of the syringe barrel 502 thereby aiding in preventing entry of contaminants into the syringe barrel cavity 502C. The sweeping and wiping action functions to push contaminants such as dirt, dust, microorganisms, and pathogens, and any other types of contaminant carried by the air, hands, fingers, gloves, etc, that are deposited onto the exposed portion of the plunger shaft 501, in a direction away from the forward end of the plunger shaft 501FT and ultimately restricting them from entering the syringe barrel cavity 502C by way of the plunger shaft 501. The contaminant shield 510 or 520 also functions to prevent deposition of dirt, lint, viral components, bacteria, germs, dust, microorganisms, pathogens, paper fibers, and any other type of contaminant carried by the air, hands, fingers, gloves, etc., from falling into the rearward end opening 502RO of the syringe barrel 502 and becoming deposited onto the internal wall surfaces 502IW of the syringe barrel cavity 502C. The contaminant shield 510 or 520 of the instant invention provides protection to the plunger shaft 501 and the internal cavity wall surfaces 502IW of the syringe barrel 502 in that contaminants deposited onto the outer surfaces 508RF and 506RF or the environmentally exposed surfaces of the second part 507 of the contaminant shield 510 or 520 will not jeopardize the sterility of the inner cavity 502C of the syringe barrel 502 holding the medication, solution, or other fluids, etc., because the contaminants cannot penetrate rearward face surfaces 506RF or 508RF of the contaminant shields 510 and 520, respectively. It is noted that the handle member 503 of syringe barrel 530 can also be provided with an extension forming a tab, knob, or handle 503T that functions as a wall for leverage to assist the user in drawing the plunger shaft 501 from the syringe cavity 502C.

Figure 12:
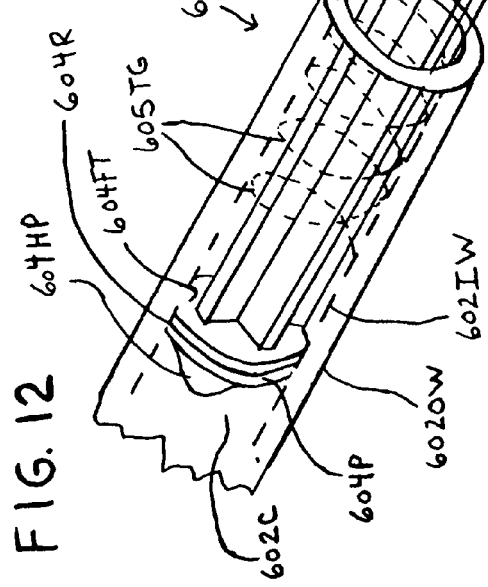
FIG. 12 is a view of a fifth embodiment of the instant invention wherein a syringe barrel section is formed with grooves at its rearward end for receiving the end cap contaminant shield having threads. A plunger shaft and piston are shown positioned within the syringe barrel cavity.

As an alternative to forming or molding the contaminant shield 510 and 520 onto the inner wall surface 502IW of the syringe barrel 502, the contaminant shield 620, as shown in FIG. 12, can be formed separately from the syringe barrel 600 and attached in a separate operation. Syringe barrel 600 has an outer wall surface 602OW and an inner wall surface 602IW. For example, the contaminant shield 620 could be formed with a male wall 607 extending perpendicularly from the forward face surface 606FF of the contaminant shield 620 with the outer surface of the male wall 607 having threads and/or grooves 608T which mate with threads and/or grooves 605TG, formed on the inner wall surfaces 602IW at or near the rearward end opening 602RO of the syringe barrel 600, by screwing, turning, twisting, or rotating the threaded and/or grooved end cap contaminant shield 620 with the threads and/or grooves 605TG on the syringe barrel 600 inner wall surface 602IW. The contaminant shield also has a rearward end face 606RF that faces the forward face surface 612 of plunger handle member 630. As an alternative, the threads and/or grooves 608T can be formed in the extending male walls 607 of the end cap contaminant shield 620 and the threads and/or grooves 605TG formed on the outer wall surfaces 602OW at the rearward end opening 602RO of the syringe barrel 600. FIG. 12 shows the plunger shaft 604PS positioned within the syringe barrel cavity 602C. The piston 604P is attached by mounting, fusing, molding, adhesives, ultrasonic bonding or welding, thermal bonding, etc., on the forward end terminus of the plunger shaft 604FT. The piston 604P has a rim 604R and a piston head 604HP. The plunger shaft 604PS has plunger shaft ribs 604PSR. The rearward terminus 604RT of the plunger shaft 604PS extends out of the rearward opening 602RO of the syringe barrel cavity 602C. One method of manufacture includes separately molding the end cap contaminant shield 620, syringe barrel 600, plunger handle member 630, and plunger shaft 604PS and piston 604P. The next steps involve assembling the syringe components. The rearward terminus 604RT of the plunger shaft 604PS is threaded through the cavity or hollow formed by the walls 607 extending from the forward face surface 606FF of the end cap contaminant shield 620 and then through the cross-sectional opening 610CSO. Upon threading of the plunger shaft 604PS through the cross-sectional opening 610CSO, the periphery of the flexible second part 609 contacts the rib surfaces 604PSR of the plunger shaft 604PS. The next step involves attachment of the plunger handle member 630 to the rear terminus 604RT of the plunger shaft 604PS. Alternatively, the plunger handle member 630 can be formed and molded directly to the rearward terminus 604RT of the plunger shaft 604PS following the threading operation such that the forward face 612 of the plunger handle member 630 is facing the rearward face surface 606RF of the end cap contaminant shield 620. The rearward face surface 611 of the plunger handle member 630 faces away from the rearward face surface 606RF of the end cap contaminant shield 620 after molding or attachment of the plunger handle member 630 to the rearward end terminus 604RT of the plunger shaft 604PS. Next, the piston 604P is attached to the plunger shaft 604PS. Alternatively, the piston 604P can be formed or molded to the plunger shaft 604PS forward end terminus 604FT prior to the threading operation or after the threading operation. Also, the piston attachment operation can occur prior to attachment of the plunger handle member 630 to the rearward terminus 604RT of the plunger shaft 604PS. Next, the plunger shaft 604PS and attached piston 604P are inserted into the syringe cavity 602C. The end cap contaminant shield 620 can then be slid along the plunger shaft 604PS such that the threads and/or grooves 608T mate with the threads and/or grooves 605TG of the syringe barrel 600 inner wall 602IW. The piston 604P, plunger shaft 604PS, end cap contaminant shield 620, and plunger handle member 630, are rotated, screwed, twisted, or turned in a clockwise direction to mate the threads and/or grooves 608T with the threads and/or grooves 605TG and cause the end cap contaminant shield 620 to be inserted into the rearward end opening 602RO of the syringe barrel 600. However, rotation of all components may not be necessary depending on the cross-section of the plunger shaft, i.e., cylindrical. A sealant or gasket material can be provided on the forward face surface 606FF of the end cap contaminant shield 620 which mates with the rear terminus 602RT surface to enhance the seal between the rear terminus wall 602RT of the syringe barrel 600 and the forward face surface 606FF of the end cap contaminant shield 620. A further alternative for attachment of the plunger shaft handle member 630 includes attaching by mounting, fusing, molding, adhesives, ultrasonic bonding or welding, thermal bonding, etc., the plunger shaft handle member 630 to the plunger shaft rear terminus 604RT following insertion, thread mating, and attachment of the end cap contaminant shield 620 to the syringe barrel 600. It is noted that the end cap contaminant shield 620 can also be provided with an extension forming a tab, knob, or handle 606 that functions as a wall for leverage to assist the user in drawing the plunger shaft 604PS from the syringe cavity 602C.

Figure 13B:
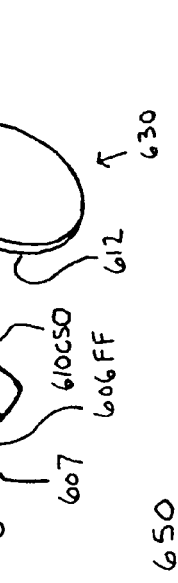
FIG. 13B is a view of an end cap contaminant shield member of the fifth embodiment without the extending wall surface as shown in FIGS. 12 and 13A. The contaminant shield member is formed of a first part with an opening, the opening having the shape of the cross-section of the plunger member. A second part is molded to the periphery of the first part at the cross-sectional opening.
Figure 13A:
FIG. 13A is a cross-sectional view of an end cap contaminant shield of the fifth embodiment formed with a lip or flange for mating with a groove formed on the inner wall surface of the syringe barrel to lock the end cap within the rearward end opening of the syringe barrel.

Further modifications, as shown in FIGS. 13A and 13B, include providing contaminant shields 640 and 650. End cap contaminant shield 640 is shown having walls 607 extending perpendicularly from the forward face surface 606FF such that the outer surface of the extended walls 607 mates with the inner wall surfaces 602IW of the syringe barrel 600 at the rearward end opening 602RO through frictional fitting, snap fitting, locking, or any combination thereof. End cap contaminant shield 640 has a lip or flange 613 extending perpendicularly from the wall 607 to facilitate fitting of the end cap contaminant shield 640 into the rearward end opening 602RO. The flange 613 mates with a complementary groove formed on the inner wall surface 602IW of the syringe barrel cavity 602C. The contaminant shield member 650 of FIG. 13B is a contaminant shield structure having all of the components of end cap contaminant shield structure 620 except for the extending walls 607 and threads and/or grooves 608T. The contaminant shield member 650 has a forward face surface 606FF and a rearward face surface 606RF. After molding of the contaminant shield 650, the forward face surface 606FF is bound or attached to the rearward end terminus 602RT of syringe barrel 600 by mounting, fusing, molding, adhesives, ultrasonic bonding or welding, thermal bonding, etc. The contaminant shield member 650 is formed of a first part material 606, which can be the same or different from the material used to form the syringe 600, and a second part material 609 having a flexible characteristic. The second part material 609 is molded to the periphery of the opening formed in the contaminant shield walls 606RF and 606FF to form a cross-sectional opening 610CSO having the cross-sectional shape of the plunger shaft 604PS. The contaminant shield member 650 is threaded over the plunger shaft 604PS prior to attachment by molding, bonding as by adhesives, ultrasonic bonding or welding, thermal bonding, etc., of the forward face surface 606FF of contaminant shield member 650 to the rearward end terminus 602RT of syringe barrel 600. The plunger handle member 630 can be molded, formed, or attached to the rearward end terminus 604RT of the plunger shaft 604PS prior to or following attachment or bonding of contaminant shield member 650 to the rearward end terminus 602RT.

An advantage of using the contaminant shield designs of the fifth embodiment is the protection provided by the shield to the internal cavity wall surfaces of the syringe in that contaminants deposited onto the rearward end wall surfaces of the shield will not jeopardize the sterility of the inner cavity of the syringe barrel because the contaminants cannot penetrate the shield.

An added function and benefit of the fifth embodiment is that the shield functions to prevent accidental separation of the plunger member from the syringe barrel by abutment of the forward face surface of the shield or the extended wall of the end cap with the forward end terminus of the plunger shaft. Second, the shield functions as a temporary dam or barrier to fluids that may escape the syringe cavity due to piston failure.

CONCLUSION

Accordingly, the reader will see that the syringes of the instant invention can be used for accomplishing many tasks requiring the use of a syringe. Because of the design of the syringes of the instant invention, entry of contaminants such as dirt, dust, microorganisms, pathogens, and any other type of contaminants, carried by air, hands, fingers, gloves, etc., which may become deposited onto the internal surfaces of the syringe barrel cavity, is discouraged. Additionally, using the syringes of the instant invention provides protection to the plunger shaft and the internal cavity wall surfaces in that contaminants deposited onto the external wall surfaces of the syringe barrel will not jeopardize the sterility of the inner cavity of the syringe barrel holding the medication, solutions, etc., or other fluid because the contaminants cannot penetrate the walls of the syringe barrel, the seals, the corrugated sheath, or the shield walls.

The syringes of the instant invention can be disposable or be reusable following an acceptable sterilization process.

The syringe barrels, plungers, plunger shafts, pistons, syringe caps, etc., of the instant invention can also have any desired geometrical and/or cross-sectional shape such as cylindrical, triangular, square, hexagonal, octagonal, etc.

The syringes and/or separate syringe components of the invention are manufactured and provided with sterile inner and outer surfaces and packaged in sterile packaging. All components are manufactured in clean room environments. Sterilization of components can be accomplished by irradiation, ethylene oxide (ETO) sterilization, etc.

The syringes, components, and materials of the instant invention are selected to meet the requirements and regulations for use, disposal, and incineration of medical devices.

The syringes of the instant invention can be of any desired shape, size, length, diameter, etc.

The syringes of the instant invention may also be manufactured having any desired color or tint, as long as the barrel retains some degree of transparency or other means to afford the user the ability to read the volume of the liquid in the syringe barrel cavity using the volume measuring indicia printed on the syringe barrel walls. The printed indicia on the syringe barrel walls provides incremental markings used to accurately measure the volume of the medication, solution, or other material drawn into the syringe barrel cavity.

The design and features of the syringes of the instant invention can be used with any volume syringe, i.e. 0.5 ml, 1 ml, 5 ml, 10 ml, 20 ml, 30 ml, 50 ml, 60 ml, etc., and any type needle, i.e., subcutaneous, filter, vented, intravenous, etc., and any size gauge needle, i.e., 18G, 19G, 21G, etc. and transfer sets, tubing, etc.

The materials used for constructing the syringes barrels, plunger members, plunger shafts, pistons, sealing rings, corrugated sheaths, needles, needle caps, handle members, contaminant shields, brace means, and other components of the instant invention include plastic materials, polymers, rubber materials, metals, alloys, glass materials, and/or combinations thereof, and any other additives necessary or desired, etc., such that the desired mechanical characteristics as disclosed herein are achieved.

The design and features of the syringes of the instant invention can be used with any type of syringe such as tuberculin, insulin, hypodermic, oral, etc.

The syringes of the instant invention can be used for withdrawing blood from patients, injecting intravenous medications into patients, operating in pump devices for delivering medications to patients, as devices for delivering medications and functioning as douches or enemas, preparing radioactive pharmaceuticals, preparing pre-filled syringes with medications for injection or oral delivery, preparing intramuscular medications for injection, preparing irrigation solutions, preparing dialysis fluids, preparing intravenous pushes, preparing bolus fluids, preparing intravenous fluids, preparing large volume parenterals for intravenous injection, and preparing oral dose medications, etc. Also, pre-filled or pre-dosed, single-use, etc., and multi-dose syringes containing injectable or oral medications can be manufactured using the syringes of the instant invention.

While the description of uses above provides many examples for use of the syringes of the instant invention, these examples should not be construed as limiting the scope of the functionality or capacity of use of the syringe designs of this invention. That is, in addition to the uses indicated above, the syringes of the instant invention can be used in any capacity which requires the use of a syringe.

The design of the sealing rings can be of any desired shape such as, circular, triangular, square, etc. The periphery forming the sealing ring can have any desired shape such as blocked, apexed, etc. The sealing rings can also be designed as flexible flaps extending from the surface of the syringe barrel and plunger member wall surfaces. Any shape locking groove, such as dovetail, etc., can be formed on the syringe barrel and plunger member walls and fitted with preformed sealing rings. Additionally, the preformed sealing rings can be formed by fusion, injection molding, or any other type of molding process, etc., or combination of processes. Alternatively, forming of the sealing rings and their attachment process or method to the syringe barrel and plunger member can be performed by injection molding or by blow molding the plunger member and syringe barrel to preformed sealing rings; or injection molding sealing rings to a preformed plunger member and syringe barrel; or, simultaneously fusing, by performing injection molding, blow molding or blow extrusion of the syringe barrel or plunger member against injection or compression molded sealing rings.

As an alternative, or in addition to the sealing rings, prongs or projections having any desired shape can be molded or formed on the syringe barrel internal wall at a desired location such that they protrude into the rib cavities and abut with the forward end terminus of the plunger shaft during its withdrawal along the syringe barrel cavity preventing complete withdrawal or separation of the plunger shaft from the syringe barrel cavity.

I claim:

1. A syringe comprising:
   a) a non-flanged hollow syringe barrel; and
   b) a plunger member comprising a plunger shaft and piston, said piston attached to said plunger shaft at the forward end terminus of said plunger shaft; and
   c) an externally attachable contaminant shield handle member comprising a single-piece contaminant shield body defined by an outer periphery and an inner terminus, said inner terminus defining an opening through said body corresponding in shape to the cross-section of said plunger shaft, said single-piece contaminant shield body comprising at least one shaped tabular handle portion, each said handle portion continuous with and substantially coplanar with said single-piece contaminant shield body; and
   d) said contaminant shield body further comprising a flexible component attached to said inner terminus of said single-piece contaminant shield body, said flexible component projecting centrally inward from said inner terminus of said opening and substantially coplanar with said single-piece contaminant shield body to define a plunger shaft passage corresponding in shape to the cross-section of said plunger shaft; and
   e) wherein said contaminant shield handle member further comprises an attachment structure extending perpendicularly from said shield body; wherein said attachment structure consists of a single wall having an external tabular flange, said single wall and said tabular flange facilitating attachment of said contaminant shield handle member to said syringe, said forward end terminus of said plunger shaft capable of abutment with said contaminant shield handle member to prevent separation of said plunger shaft from said syringe barrel;
   f) optionally, said syringe comprising coloring or tinting;
   g) optionally, said syringe comprising measuring indicia;
   h) optionally, said contaminant shield comprising coloring or tinting.

2. The syringe of claim 1, wherein said shaped tabular handle portion assists in advancement and withdrawal of said plunger member.

3. The syringe of claim 1, wherein said tabular flange mates with syringe barrel grooves in the wall surface of the syringe barrel.

4. The syringe of claim 1, wherein said flexible component contacts and is capable of providing a sweeping and wiping action to said plunger shaft during advancement and withdrawal of said plunger member.

5. The syringe of claim 1, wherein said plunger shaft is capable of advancing and withdrawing said piston along said hollow syringe barrel.

6. The contaminant shield handle member of claim 1, wherein said plunger shaft and the inner wall surfaces of said perpendicularly extending wall have an unobstructed face-to-face relationship from the forward terminus of said perpendicularly extending wall to the rear terminus of said perpendicularly extending wall.

7. The syringe of claim 1, wherein said single-piece contaminant shield handle member body and said flexible component are external to said syringe following said attachment, and wherein the external wall surface of the syringe barrel is unobstructed by said attachment structure and said contaminant shield handle member.

8. A contaminant shield handle member for use with a syringe comprising a plunger shaft wherein the contaminant shield handle member comprises:
   a) a single-piece contaminant shield body defined by an outer periphery and an inner terminus defining an opening through said contaminant shield body corresponding in shape to the cross-section of said plunger shaft, said contaminant shield body comprising a central body portion and at least one shaped tabular handle portion, each said tabular handle portion continuous with and substantially coplanar with said central body portion; and
   b) a flexible second part component, said second part lockingly attached along the entire length of the inner terminus of said single-piece contaminant shield body, said second part extending centrally inward from said inner terminus and coplanarly with said single-piece contaminant shield body to terminate as a passage corresponding in shape to the cross-section of said plunger shaft;
   c) wherein said contaminant shield handle member further comprises an attachment structure extending perpendicularly from said shield body, wherein said attachment structure consists of a single wall having an external tabular flange, said single wall facilitating attachment of said contaminant shield handle member to said syringe, wherein the external wall surface of the syringe barrel is unobstructed by said attachment structure and said contaminant shield handle member; and
   d) optionally, said shield handle member comprising coloring or tinting.

9. The contaminant shield handle member of claim 8, wherein said at least one shaped tabular handle portion assists in advancement and withdrawal of said plunger shaft.

10. The contaminant shield handle member of claim 8, wherein said flexible second part component of said shield contacts and is capable of providing a sweeping and wiping action to said plunger shaft during advancement and withdrawal of said plunger shaft.

11. The contaminant shield handle member of claim 8, wherein said single-piece contaminant shield handle member body and said flexible component are external to said syringe following said attachment.

12. The contaminant shield handle member of claim 8, wherein said external tabular flange mates with grooves formed in the inner wall surface of said syringe barrel.

13. A syringe comprising:
   a) a hollow syringe barrel; and
   b) a plunger member comprising a plunger shaft with an attached piston, said plunger member non-separable from said syringe barrel; and
   c) a contaminant shield handle member comprising a single-piece contaminant shield body defined by an outer periphery and an inner terminus, said inner terminus defining an opening through said single-piece contaminant shield body corresponding in shape to the cross-section of said plunger shaft; said single-piece contaminant shield body having a front face and a rear face; said single-piece contaminant shield body comprising at least one shaped tabular handle portion, each said handle portion continuous with and extending coplanarly with said single-piece contaminant shield body; said contaminant shield handle member further comprising a flexible component lockingly attached to said inner terminus of said single-piece contaminant shield body; said flexible component extending centrally inward of said opening and coplanarly with said contaminant shield body to terminate as a passage for said plunger shaft and corresponding in shape to the cross-section of said plunger shaft; and
   d) wherein said contaminant shield handle member further comprises an attachment structure extending perpendicularly from said front face of said single-piece contaminant shield body; wherein said attachment structure consists of a single wall having an external tabular flange, said single wall and said tabular flange facilitating attachment of said contaminant shield handle member to said syringe; and
   e) optionally, said syringe comprising coloring or tinting;
   f) optionally, said contaminant shield comprising coloring or tinting;
   g) optionally, said syringe comprising measuring indicia.

14. The syringe of claim 13, wherein said syringe barrel comprises grooves for mating with said tabular flange.

15. The syringe of claim 13, wherein said plunger shaft and the inner wall surfaces of said perpendicularly extending wall have an unobstructed face-to-face relationship from the forward terminus of said perpendicularly extending wall to the rear terminus of said perpendicularly extending wall, and wherein the external wall surface of the syringe barrel is unobstructed by said attachment structure and said contaminant shield handle member.

16. The syringe of claim 8, wherein said contaminant shield handle member comprises a sealant or gasket material attached at the forward face surface of said single-piece contaminant shield body.

17. The syringe of claim 13, wherein said at least one shaped tabular handle portion assists in advancement and withdrawal of said plunger member.

18. The syringe of claim 13, wherein said flexible component contacts and is capable of providing a sweeping and wiping action to said plunger shaft during advancement and withdrawal of said plunger member.

19. The contaminant shield handle member of claim 13, wherein said plunger shaft is capable of advancing and withdrawing said piston along said hollow syringe barrel.

20. A contaminant shield for use with a syringe comprising a plunger shaft wherein the contaminant shield comprises:
   a) a first part defined by a rigid single-piece contaminant shield body comprising at least one shaped tabular handle member portion, each said handle member continuous with and extending substantially coplanar with said single-piece contaminant shield body, said single-piece contaminant shield body having an opening centrally formed therethrough defining an inner continuous periphery corresponding in shape to the cross-section of said plunger shaft, said single-piece contaminant shield body having a front face and a rear face; and
   b) a flexible second part attached at said periphery, said flexible second part extending centrally inward from said periphery into said opening and being substantially coplanar with said single-piece contaminant shield body to terminate as a shaped passage corresponding in shape to the cross-section of said plunger shaft; and
   c) said contaminant shield comprising an attachment structure extending perpendicularly from said front face of said single-piece contaminant shield body, said attachment structure consists of single wall having a tabular lip extending from said single wall to facilitate attachment of said contaminant shield to a syringe barrel, and wherein the external wall surface of the syringe barrel is unobstructed by said attachment structure and said contaminant shield handle member; and
   d) optionally, said shield comprising a sealant or gasket material;
   e) optionally, said syringe and/or shield comprising coloring or tinting.

* * * * *